(12) United States Patent
Terliuc et al.

(10) Patent No.: US 10,314,471 B2
(45) Date of Patent: Jun. 11, 2019

(54) ENDOSCOPE REPROCESSING METHOD

(71) Applicant: SMART MEDICAL SYSTEMS LTD., Raanana (IL)

(72) Inventors: Gad Terliuc, Raanana (IL); Gilad Luria, Givataim (IL); Erez Hochman, Tel Aviv (IL)

(73) Assignee: SMART Medical Systems Ltd., Ra'anana (IL)

( * ) Notice: Subject to any disclaimer, the term of this patent is extended or adjusted under 35 U.S.C. 154(b) by 92 days.

(21) Appl. No.: 14/891,683

(22) PCT Filed: May 21, 2014

(86) PCT No.: PCT/IL2014/000025
§ 371 (c)(1),
(2) Date: Nov. 17, 2015

(87) PCT Pub. No.: WO2014/188402
PCT Pub. Date: Nov. 27, 2014

(65) Prior Publication Data
US 2016/0095508 A1 Apr. 7, 2016

Related U.S. Application Data

(60) Provisional application No. 61/855,688, filed on May 21, 2013, provisional application No. 61/962,383, filed on Nov. 6, 2013.

(51) Int. Cl.
*A61L 2/18* (2006.01)
*A61B 1/12* (2006.01)
(Continued)

(52) U.S. Cl.
CPC .......... *A61B 1/123* (2013.01); *A61B 1/00057* (2013.01); *A61B 1/00082* (2013.01);
(Continued)

(58) Field of Classification Search
CPC ......... B08B 5/00; B08B 5/04; A61B 1/00082; A61B 1/00119; A61B 1/015; A61B 1/123;
(Continued)

(56) References Cited

U.S. PATENT DOCUMENTS 3,837,347 A 9/1974 Tower
3,884,242 A 5/1975 Bazell et al.
(Continued)

FOREIGN PATENT DOCUMENTS

CN 1394543 2/2003
CN 2624936 7/2004
(Continued)

OTHER PUBLICATIONS

An International Search Report and a Written Opinion both dated Oct. 18, 2011, which issued during the prosecution of Applicant's PCT/IL2011/000222.
(Continued)

*Primary Examiner* — Katelyn B Whatley
(74) *Attorney, Agent, or Firm* — Knobbe, Martens, Olson & Bear, LLP

(57) ABSTRACT

A method for reprocessing a balloon endoscope, the method including the steps of deflating a balloon of a balloon endoscope to a negative pressure state following clinical use thereof and thereafter maintaining the interior of the balloon in a negative pressure state during at least part of reprocessing the balloon endoscope.

23 Claims, 18 Drawing Sheets

(51) Int. Cl.
 *A61B 1/00* (2006.01)
 *A61B 1/015* (2006.01)
 *A61B 1/31* (2006.01)
 *G01M 3/32* (2006.01)

(52) U.S. Cl.
 CPC .......... *A61B 1/00119* (2013.01); *A61B 1/015* (2013.01); *A61B 1/125* (2013.01); *A61B 1/31* (2013.01); *A61L 2/18* (2013.01); *G01M 3/3272* (2013.01); *A61B 1/00059* (2013.01); *A61M 2205/15* (2013.01)

(58) Field of Classification Search
 CPC . A61B 1/125; A61B 1/31; A61L 2/18; A61M 2205/15
 See application file for complete search history.

(56) References Cited

U.S. PATENT DOCUMENTS

| | | | |
|---|---|---|---|
| 3,895,637 A | 7/1975 | Choy | |
| 4,040,413 A | 8/1977 | Ohshiro | |
| 4,148,307 A | 4/1979 | Utsugi | |
| 4,176,662 A | 12/1979 | Frazer | |
| 4,195,637 A | 4/1980 | Gruntzig et al. | |
| 4,224,929 A | 9/1980 | Furihata | |
| 4,261,339 A | 4/1981 | Hanson et al. | |
| 4,351,341 A | 9/1982 | Goldberg et al. | |
| 4,444,188 A | 4/1984 | Bazell et al. | |
| 4,453,545 A | 6/1984 | Inoue | |
| 4,616,652 A | 10/1986 | Simpson | |
| 4,676,228 A | 6/1987 | Krasner et al. | |
| 4,681,093 A | 7/1987 | Ono et al. | |
| 4,690,131 A | 9/1987 | Lyddy et al. | |
| 4,721,123 A * | 1/1988 | Cosentino ........... | A61M 25/002 134/113 |
| 4,862,874 A | 9/1989 | Kellner | |
| 4,917,088 A | 4/1990 | Crittenden | |
| 5,135,487 A | 8/1992 | Morrill et al. | |
| 5,259,366 A | 11/1993 | Reydel et al. | |
| 5,310,524 A | 5/1994 | Campbell et al. | |
| 5,338,299 A | 8/1994 | Barlow | |
| 5,411,016 A | 5/1995 | Kume et al. | |
| 5,445,646 A | 8/1995 | Euteneuer et al. | |
| 5,454,364 A | 10/1995 | Kruger | |
| 5,569,220 A | 10/1996 | Webster, Jr. | |
| 5,593,419 A | 1/1997 | Segar | |
| 5,607,441 A | 3/1997 | Sierocuk et al. | |
| 5,653,240 A | 8/1997 | Zimmon | |
| 5,693,014 A | 12/1997 | Abele et al. | |
| 5,700,242 A | 12/1997 | Mulder | |
| 5,707,382 A | 1/1998 | Sierocuk et al. | |
| 5,707,392 A | 1/1998 | Kortenbach | |
| 5,823,940 A | 10/1998 | Newman | |
| 5,851,477 A | 12/1998 | Halgren et al. | |
| 5,904,701 A | 5/1999 | Daneshvar | |
| 5,984,860 A | 11/1999 | Shan | |
| 6,007,482 A | 12/1999 | Madni et al. | |
| 6,162,171 A | 12/2000 | Ng et al. | |
| 6,261,260 B1 | 7/2001 | Maki et al. | |
| 6,412,334 B1 | 7/2002 | Kral | |
| 6,461,294 B1 | 10/2002 | Oneda et al. | |
| 6,485,684 B1 | 11/2002 | Mapson et al. | |
| 6,585,639 B1 | 7/2003 | Kotmel et al. | |
| 6,589,208 B2 | 7/2003 | Ewers et al. | |
| 6,663,589 B1 | 12/2003 | Halevy | |
| 6,695,810 B2 | 2/2004 | Peacock, III et al. | |
| 6,702,735 B2 | 3/2004 | Kelly | |
| 6,764,441 B2 | 7/2004 | Chiel et al. | |
| 6,986,736 B2 | 1/2006 | Williams et al. | |
| 7,081,096 B2 | 7/2006 | Brister et al. | |
| 7,169,140 B1 | 1/2007 | Kume | |
| 7,635,346 B2 | 12/2009 | Cabiri et al. | |
| 7,695,428 B2 | 4/2010 | Machida | |
| 7,699,771 B2 | 4/2010 | Wendlandt | |
| 7,713,191 B2 | 5/2010 | Sekiguchi et al. | |
| 7,837,672 B2 | 11/2010 | Intoccia | |
| 7,887,480 B2 | 2/2011 | Sekiguchi | |
| 7,918,788 B2 | 4/2011 | Lin et al. | |
| 7,963,911 B2 | 6/2011 | Terliuc | |
| 8,002,698 B2 | 8/2011 | Motai et al. | |
| 8,012,084 B2 | 9/2011 | Machida | |
| 8,152,715 B2 | 4/2012 | Root et al. | |
| 8,187,221 B2 | 5/2012 | Bates | |
| 8,197,463 B2 | 6/2012 | Intoccia | |
| 8,273,013 B2 | 9/2012 | Niwa et al. | |
| 8,419,678 B2 | 4/2013 | Cabiri et al. | |
| 8,480,572 B2 | 7/2013 | Ishigami | |
| 8,545,382 B2 | 10/2013 | Suzuki et al. | |
| 8,727,970 B2 | 5/2014 | Terliuc et al. | |
| 8,939,895 B2 | 1/2015 | Simchony et al. | |
| 9,119,532 B2 | 9/2015 | Terliuc et al. | |
| 9,278,202 B2 | 3/2016 | Ranade | |
| 9,427,142 B2 | 8/2016 | Terliuc | |
| 9,480,390 B2 | 11/2016 | Farhadi | |
| 9,511,209 B2 | 12/2016 | Drasler et al. | |
| 9,521,945 B2 | 12/2016 | Farhadi | |
| 9,596,979 B2 | 3/2017 | Terliuc et al. | |
| 9,604,042 B2 | 3/2017 | Fox et al. | |
| 9,661,994 B2 | 5/2017 | Terliuc et al. | |
| 10,052,014 B2 | 8/2018 | Terliuc et al. | |
| 2001/0032494 A1 | 10/2001 | Greszler | |
| 2002/0147385 A1 | 10/2002 | Butler et al. | |
| 2003/0074015 A1 | 4/2003 | Nakao | |
| 2003/0236495 A1 | 12/2003 | Kennedy | |
| 2004/0102681 A1 | 5/2004 | Gross | |
| 2004/0210116 A1 | 10/2004 | Nakao | |
| 2004/0236366 A1 | 11/2004 | Kennedy et al. | |
| 2005/0027253 A1 | 2/2005 | Castellano et al. | |
| 2005/0124856 A1 | 6/2005 | Fujikura et al. | |
| 2005/0125005 A1 | 6/2005 | Fujikura | |
| 2005/0133453 A1 | 6/2005 | Woodruff et al. | |
| 2005/0137457 A1 | 6/2005 | Machida | |
| 2005/0165233 A1 | 7/2005 | Hamedi et al. | |
| 2005/0165273 A1 | 7/2005 | Takano | |
| 2005/0171400 A1 | 8/2005 | Itoi | |
| 2006/0095063 A1 | 5/2006 | Sekiguchi | |
| 2006/0100480 A1 | 5/2006 | Ewers et al. | |
| 2006/0111610 A1 | 5/2006 | Machida | |
| 2006/0116549 A1 | 6/2006 | Sekiguchi et al. | |
| 2006/0161044 A1 | 7/2006 | Oneda et al. | |
| 2006/0282088 A1 | 12/2006 | Ryan | |
| 2007/0010785 A1 | 1/2007 | Sekiguchi et al. | |
| 2007/0038026 A1 | 2/2007 | Yoshida et al. | |
| 2007/0083158 A1 | 4/2007 | Hirszowicz et al. | |
| 2007/0185385 A1 | 8/2007 | Noguchi et al. | |
| 2007/0213586 A1 | 9/2007 | Hirose et al. | |
| 2007/0244361 A1 | 10/2007 | Ikeda et al. | |
| 2007/0276181 A1 | 11/2007 | Terliuc | |
| 2008/0009673 A1 | 1/2008 | Khachi | |
| 2008/0161645 A1 | 7/2008 | Goldwasser et al. | |
| 2008/0177142 A1 | 7/2008 | Roskopf | |
| 2008/0306441 A1 | 12/2008 | Brown et al. | |
| 2009/0012469 A1 | 1/2009 | Nita | |
| 2009/0018500 A1 | 1/2009 | Carter et al. | |
| 2009/0048483 A1 | 2/2009 | Yamamoto | |
| 2009/0156896 A1 | 6/2009 | Kura | |
| 2009/0187069 A1 | 7/2009 | Terliuc | |
| 2009/0287058 A1 | 11/2009 | Terliuc | |
| 2010/0041951 A1 | 2/2010 | Glozman et al. | |
| 2010/0042046 A1 | 2/2010 | Chang et al. | |
| 2010/0217185 A1 | 8/2010 | Terliuc et al. | |
| 2012/0178994 A1 | 7/2012 | Schembre | |
| 2012/0232342 A1 | 9/2012 | Reydel | |
| 2012/0285488 A1 | 11/2012 | Labib et al. | |
| 2013/0023920 A1* | 1/2013 | Terliuc ............... | A61B 1/00057 606/192 |
| 2013/0090527 A1 | 4/2013 | Axon | |
| 2013/0116549 A1 | 5/2013 | Gunday | |
| 2014/0088362 A1 | 3/2014 | Terliuc et al. | |
| 2014/0155696 A1 | 6/2014 | Sakata | |
| 2015/0073216 A1 | 3/2015 | Papay | |
| 2015/0273191 A1 | 10/2015 | Terliuc et al. | |
| 2015/0335229 A1 | 11/2015 | Terliuc | |

(56) References Cited

U.S. PATENT DOCUMENTS

| | | | |
|---|---|---|---|
| 2016/0022120 | A1 | 1/2016 | Terliuc et al. |
| 2016/0081536 | A1 | 3/2016 | Farhadi |
| 2016/0095508 | A1 | 4/2016 | Terliuc et al. |
| 2017/0027415 | A1 | 2/2017 | Terliuc et al. |
| 2017/0027433 | A1 | 2/2017 | Terliuc |
| 2017/0065155 | A1 | 3/2017 | Farhadi |
| 2017/0100017 | A1 | 4/2017 | Terliuc et al. |
| 2017/0203080 | A1 | 7/2017 | Terliuc et al. |
| 2017/0360282 | A1 | 12/2017 | Terliuc et al. |

FOREIGN PATENT DOCUMENTS

| | | |
|---|---|---|
| CN | 1550203 | 12/2004 |
| CN | 1636502 | 7/2005 |
| CN | 1647747 | 8/2005 |
| CN | 1649630 | 8/2005 |
| CN | 1827031 | 9/2006 |
| CN | 1917802 | 2/2007 |
| CN | 1933766 | 3/2007 |
| CN | 1946328 | 4/2007 |
| CN | 1951312 | 4/2007 |
| CN | 101015440 | 8/2007 |
| CN | 101103898 | 1/2008 |
| CN | 101243965 | 8/2008 |
| CN | 101347321 | 1/2009 |
| CN | 101380220 | 3/2009 |
| CN | 101396256 | 4/2009 |
| CN | 101522091 | 9/2009 |
| CN | 101541227 | 9/2009 |
| CN | 101664560 | 3/2010 |
| CN | 102791180 | 11/2012 |
| CN | 103269638 | 8/2013 |
| DE | 4317601 A1 | 12/1994 |
| DE | 10209993 A1 | 4/2003 |
| EP | 0 212 696 | 3/1987 |
| EP | 0473045 A1 | 3/1995 |
| EP | 0733342 | 9/1996 |
| EP | 1433410 | 6/2004 |
| EP | 1547641 | 6/2005 |
| EP | 1551316 B1 | 7/2005 |
| EP | 1656879 | 5/2006 |
| EP | 1556118 B1 | 12/2006 |
| EP | 1726248 B1 | 12/2010 |
| EP | 1335659 B1 | 4/2011 |
| EP | 2320984 B1 | 5/2011 |
| EP | 2110068 B1 | 8/2011 |
| EP | 1706169 B1 | 5/2015 |
| JP | SHO50-016762 | 2/1975 |
| JP | S57-57804 | 4/1982 |
| JP | S61202274 | 9/1986 |
| JP | SHO61-284226 | 12/1986 |
| JP | SHO62-002925 | 1/1987 |
| JP | SHO63-102429 | 7/1988 |
| JP | SHO64-017203 | 1/1989 |
| JP | H2-58402 | 4/1990 |
| JP | H04-102436 | 4/1992 |
| JP | H04-297219 | 10/1992 |
| JP | HEI 05337081 | 12/1993 |
| JP | H06-63045 | 3/1994 |
| JP | HEI6-339455 | 12/1994 |
| JP | HEI7-12101 | 2/1995 |
| JP | HEI7-148105 | 6/1995 |
| JP | H08228996 | 9/1996 |
| JP | HEI10-127571 | 5/1998 |
| JP | HEI10-286309 | 10/1998 |
| JP | HEI11-225947 | 8/1999 |
| JP | 2000-060793 | 2/2000 |
| JP | 2000-329534 | 11/2000 |
| JP | 2002-34900 | 2/2002 |
| JP | 2002-301019 | 10/2002 |
| JP | 2003-275173 | 9/2003 |
| JP | 2003250896 | 9/2003 |
| JP | 2004-97718 | 4/2004 |
| JP | 2004-329720 | 11/2004 |
| JP | 2005-185704 | 7/2005 |
| JP | 2005-185706 | 7/2005 |
| JP | 2005-185707 | 7/2005 |
| JP | 2005-279128 | 10/2005 |
| JP | 2005296256 | 10/2005 |
| JP | 2005-334475 | 12/2005 |
| JP | 2006130014 | 5/2006 |
| JP | 2006-167310 | 6/2006 |
| JP | 2006-304906 | 11/2006 |
| JP | 2006-334149 | 12/2006 |
| JP | 2007-014475 | 1/2007 |
| JP | 2007-026814 | 2/2007 |
| JP | 2007-130082 | 5/2007 |
| JP | 2007-517576 | 7/2007 |
| JP | 2007-521907 | 8/2007 |
| JP | 2007-268137 | 10/2007 |
| JP | 2007-268147 | 10/2007 |
| JP | 2007-296054 | 11/2007 |
| JP | 2008-006000 | 1/2008 |
| JP | 2008125886 | 6/2008 |
| JP | 2008-537493 | 9/2008 |
| JP | 2009-056121 | 3/2009 |
| JP | 2009-195321 | 9/2009 |
| JP | 2009-537212 | 10/2009 |
| JP | 2009-254554 | 11/2009 |
| JP | 2012504431 | 4/2010 |
| WO | 96/00099 | 1/1996 |
| WO | 98/30249 | 7/1998 |
| WO | 02/094087 | 11/2002 |
| WO | 2005/017854 | 2/2005 |
| WO | 2005/074377 | 8/2005 |
| WO | 2005/089625 | 9/2005 |
| WO | WO 2006/123590 A1 | 11/2006 |
| WO | 2007/023492 | 3/2007 |
| WO | 2007/135665 | 11/2007 |
| WO | 2008/004228 | 1/2008 |
| WO | WO 2008/073126 A1 | 6/2008 |
| WO | WO 2008/121143 A1 | 10/2008 |
| WO | 2008/142685 | 11/2008 |
| WO | 2009/122395 | 10/2009 |
| WO | 2010/046891 | 4/2010 |
| WO | WO 2010/070291 A2 | 6/2010 |
| WO | 2010/137025 | 12/2010 |
| WO | 2011/111040 | 9/2011 |
| WO | 2014/188402 | 11/2014 |
| WO | WO 2014/188402 A1 | 11/2014 |
| WO | WO 2015/160970 A1 | 10/2015 |

OTHER PUBLICATIONS

An International Preliminary Report on Patentability dated Sep. 11, 2012, which issued during the prosecution of Applicant's PCT/IL2011/000222.
An Office Action dated Mar. 16, 2017, which issued during the prosecution of Chinese Patent Application No. 201410483767.9.
An Office Action dated Jun. 25, 2015, which issued during the prosecution of U.S. Appl. No. 13/583,634.
An Office Action dated Apr. 3, 2015, which issued during the prosecution of Japanese Patent Application No. 2012-556642.
An Office Action dated Sep. 16, 2016, which issued during the prosecution of Japanese Patent Application No. 2015-175589.
An Office Action dated Jul. 20, 2016, which issued during the prosecution of Chinese Patent Application No. 201510483785.7.
An Office Action dated May 24, 2017, which issued during the prosecution of Chinese Patent Application No. 201510483785.7.
An Office Action dated Jun. 3, 2016, which issued during the prosecution of Chinese Patent Application No. 201410484557.1.
An Office Action dated Mar. 15, 2017, which issued during the prosecution of Chinese Patent Application No. 201410484557.1.
An Office Action dated Jun. 1, 2016, which issued during the prosecution of Chinese Patent Application No. 201510484559.0.
An Office Action dated Mar. 20, 2017, which issued during the prosecution of Chinese Patent Application No. 201510483997.5.
An Office Action dated Feb. 22, 2017, which issued during the prosecution of U.S. Appl. No. 13/583,634.
European Search Report dated Jul. 16, 2014, which issued during the prosecution of Applicant's European App No. 12754885.7.

(56) References Cited

OTHER PUBLICATIONS

Evis Exera II CLV-180 product brochure, http://www.olympus.nl/medical/en/medical_systems/hidden/downloadJsp.jsp?link=/medical/rmt/media/content/content 1/documents 1/brochures 1/EVIS_EXERA_ll_CLV-180_product_brochure_001_V1-en_GB_20000101.pdf, [online].
BS-2 Front Balloon, http://www.fujifilmusa.com/products/medical/endoscopy/endoscopes/specialized-balloons-andovertube/index.html#balloonsspecifications, [online].
An Office Action dated Jan. 30, 2017, which issued during the prosecution of Canadian Patent Application No. 2,791,838.
An Office Action dated Jun. 14, 2016, which issued during the prosecution of U.S. Appl. No. 13/583,634.
An Office Action dated Nov. 5, 2014, which issued during the prosecution of U.S. Appl. No. 13/583,634.
An Office Action dated May 24, 2016, which issued during the prosecution of Chinese Patent Application No. 201510483997.5.
An Office Action dated Sep. 3, 2015, which issued during the prosecution of Israel Patent Application No. 221621.
An Office Action dated Nov. 14, 2016, which issued during the prosecution of Israel Patent Application No. 228174.
Notice of Allowance dated May 28, 2015, which issued during the prosecution of Chinese Patent Application No. 2011/0013002.9.
An Office Action dated Feb. 1, 2016, which issued during the prosecution of Australian Patent Application No. 2011225671.
Notice of Allowance dated Feb. 10, 2017, which issued during the prosecution of Australian Patent Application No. 2011225671.
Single Balloon Endoscope: Balloon pump control OBCU: http://medical.olympusamerica.com/products/control/ballooncontrol-unit-obcu,[online].
Single Balloon Endoscope: SIF-Q 1 80 enteroscope: http://medical.olympusamerica.com/products/enteroscope/evisexera-ii-sif-q180,[online].
An Office Action dated Jan. 21, 2016, which issued during the prosecution of Canadian Patent Application No. 2,791,838.
U.S. Appl. No. 61/962,383, filed Nov. 6, 2013.
A communication from the European Patent Office dated Jul. 23, 2015, which issued during the prosecution of European Application No. 12754885.7.
An Office Action dated Nov. 22, 2016, which issued during the prosecution of U.S. Appl. No. 14/003,799.
Office Action dated Mar. 18, 2015, which issued during the prosecution of U.S. Appl. No. 14/003,799.
An Office Action dated May 9, 2016, which issued during the prosecution of U.S. Appl. No. 14/003,799.
An Office Action dated Oct. 7, 2015, which issued during the prosecution of U.S. Appl. No. 14/003,799.
An Office Action dated Mar. 28, 2017 which issued during the prosecution of U.S. Appl. No. 14/003,799.
A communication from the European Patent Office dated Jul. 6, 2016, which issued during the prosecution of European Application No. 12754885.7.
A communication from the European Patent Office dated May 17, 2017, which issued during the prosecution of European Application No. 12754885.7.
An Office Action dated Apr. 25, 2016, which issued during the prosecution of Chinese Patent Application No. 201510484558.6.
Notice of Allowance dated Mar. 10, 2017, which issued during the prosecution of Chinese Patent Application No. 201510484558.6.
An International Search Report and a Written Opinion both dated Jul. 13, 2012, which issued during the prosecution of Applicant's PCT/IL12/00003.
An International Preliminary Report on Patentability dated Sep. 10, 2013, which issued during the prosecution of Applicant's PCT/IL12/00003.
An Office Action dated Mar. 13, 2017, which issued during the prosecution of Chinese Patent Application No. 201510484566.0.
An Office Action dated Apr. 25, 2016, which issued during the prosecution of Chinese Patent Application No. 201510484566.0.
An Office Action dated Mar. 20, 2017, which issued during the prosecution of Chinese Patent Application No. 201510484559.0.
An Office Action dated Feb. 11, 2015, which issued during the prosecution of Chinese Patent Application No. 2011/0013002.9.
An Office Action dated Aug. 4, 2014, which issued during the prosecution of Chinese Patent Application No. 2011/0013002.9.
Double Balloon Endoscope: EC-450B15 colonoscope: http://www.fujifilmusa.com/products/medical/endoscopy/endoscopes/enteroscopes/index.html,[online].
Double Balloon Endoscope: Balloon pump controller BP-30: http://www.fujifilmusa.com/products/medical/endoscopy/endoscopes/balloon-pump-controller/index.html, [online].
Double Balloon Endoscope: EPX-4440HD video system: http://www.fujifilmusa.com/products/medical/endoscopy/video-systems/epx-4440hd, [online].
Double Balloon Endoscope: TS-13 101 overtube: http://www.fujifilmusa.com/products/medical/endoscopy/endoscopes/specialized-balloons-and-overtube/index.html, [online].
Single Balloon Endoscope: ST-SB 1 overtube: http://medical.olympusamerica.com/products/tubes/single-use-st-sb11, [online].
U.S. Appl. No. 61/855,688, filed May 21, 2013.
An Office Action dated Apr. 15, 2016, which issued during the prosecution of Chinese Patent Application No. 201280022024.6.
An Office Action dated May 26, 2015, which issued during the prosecution of Chinese Patent Application No. 201280022024.6.
An Office Action dated Nov. 1, 2016, which issued during the prosecution of Chinese Patent Application No. 201280022024.6.
An Office Action dated Dec. 9, 2016, which issued during the prosecution of Australian Patent Application No. 2012226390.
Notice of Allowance dated Dec. 22, 2016 which issued during the prosecution of Australian Patent Application No. 2012226390.
An Office Action dated Oct. 27, 2015, which issued during the prosecution of Japanese Patent Application No. 2013-557219.
An Office Action dated Oct. 24, 2016, which issued during the prosecution of Japanese Patent Application No. 2013-557219.
An Office Action dated Dec. 28, 2015, which issued during the prosecution of Japanese Patent Application No. 2015-004799.
An Office Action dated Dec. 6, 2016, which issued during the prosecution of Japanese Patent Application No. 2015-004799.
An Office Action dated Apr. 4, 2014, which issued during the prosecution of U.S. Appl. No. 13/583,634.
An Office Action dated Dec. 15, 2015, which issued during the prosecution of Australian Patent Application No. 2012226390.
An International Search Report and a Written Opinion both dated Sep. 4, 2014, which issued during the prosecution of Applicant's PCT/IL2014/000025.
An International Preliminary Report on Patentability dated Nov. 24, 2015, which issued during the prosecution of Applicant's PCT/IL2014/000025.
European Search Report dated Jan. 4, 2017, which issued during the prosecution of Applicant's European App No. 14800390.8.
An Office Action dated Dec. 9, 2016, which issued during the prosecution of Chinese Patent Application No. 201480029252.5.
European Search Report dated Apr. 8, 2014, which issued during the prosecution of Applicant's European App No. 11752941.2.
An Office Action dated May 25, 2016, which issued during the prosecution of Chinese Patent Application No. 201410483767.9.
Office Action in AU 2014269901 dated Jan. 12, 2018.
Office Action in AU 2017202285 dated Jan. 4, 2018.
Office Action in CA 2,791,838 dated Dec. 15, 2017.
Notice of Allowance in CN 201510483785.7 dated Sep. 26, 2017.
Notice of Allowance in CN 201510484557.1 dated Aug. 24, 2017.
Office Action in CN 201510483997.5 dated Sep. 28, 2017.
Office Action in CN 2,828,608 dated Jul. 18, 2017.
Office Action in CN 201280022024.6 dated Jul. 5, 2017.
Office Action in CN 201480029252.5 dated Nov. 1, 2017.
Office Action in CN 201510483767.9 dated Nov. 27, 2017.
Office Action in CN 201510484559.0 dated Dec. 14, 2017.
Office Action in CN 201510484566.0 dated Oct. 20, 2017.
Office Action in EP 11752941.2 dated Feb. 6, 2018.
Office Action in JP 2016514529 dated Feb. 9, 2018.
Office Action in JP 2017012628 dated Feb. 26, 2018.
Office Action in JP 2016189043 dated Jun. 28, 2017.

(56) References Cited

OTHER PUBLICATIONS

Office Action in U.S. Appl. No. 14/003,799 dated Oct. 5, 2017.
Office Action in U.S. Appl. No. 13/583,634 dated Oct. 2, 2017.
Office Action in U.S. Appl. No. 14/003,799 dated Mar. 27, 2018.

* cited by examiner

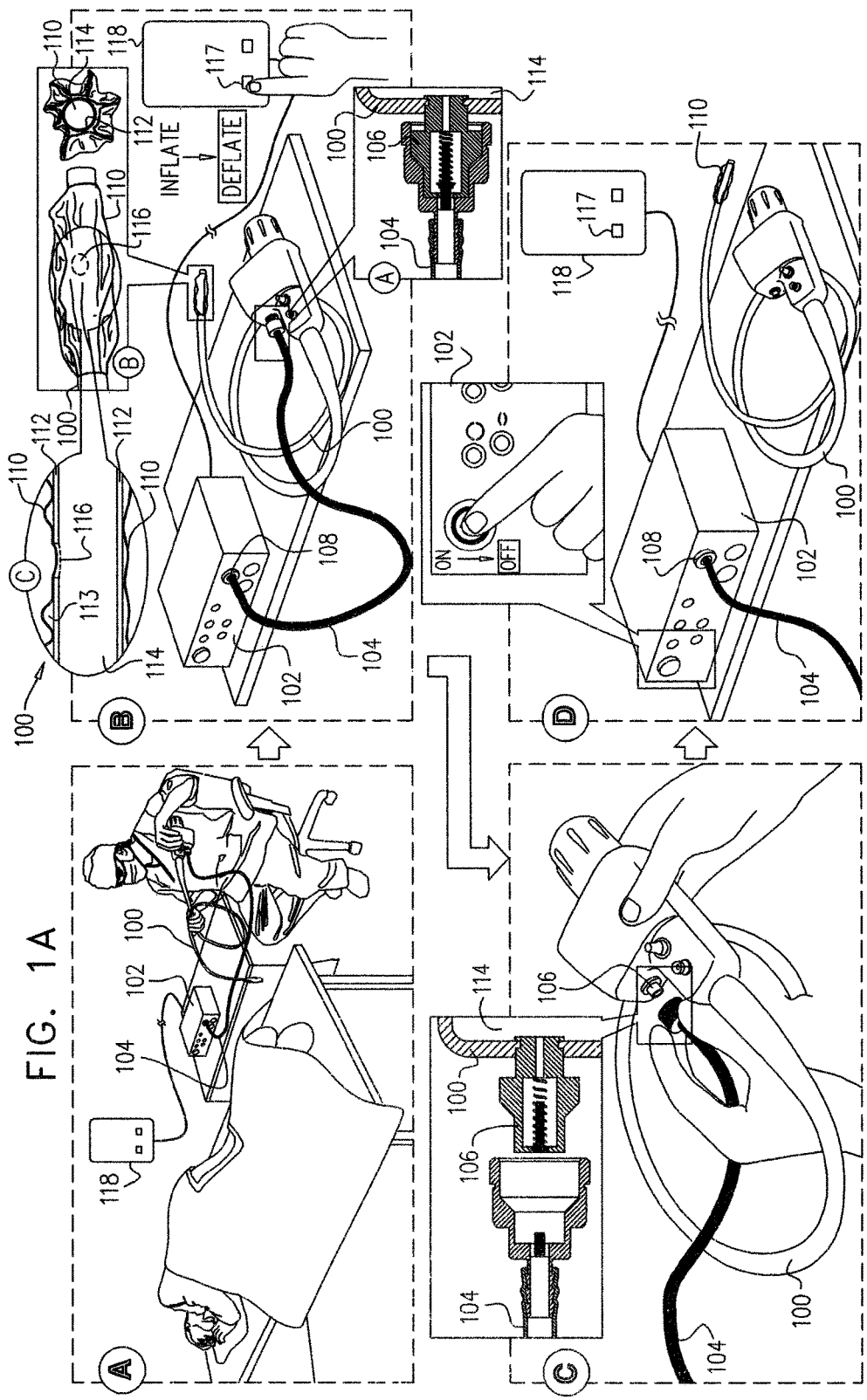

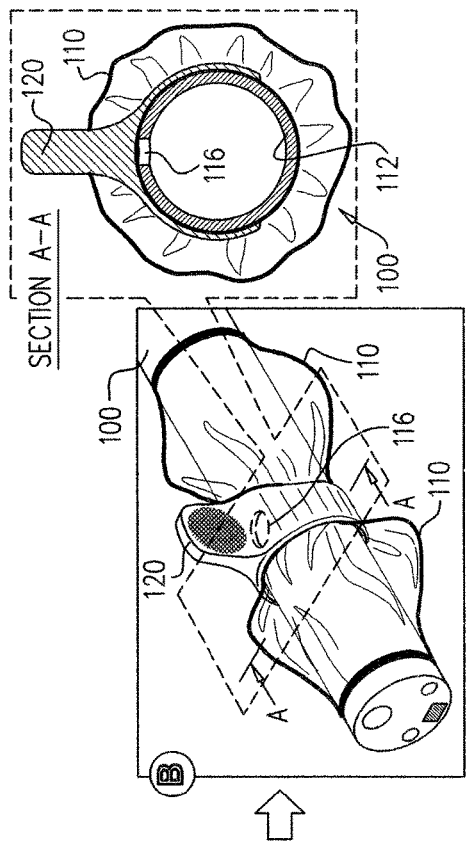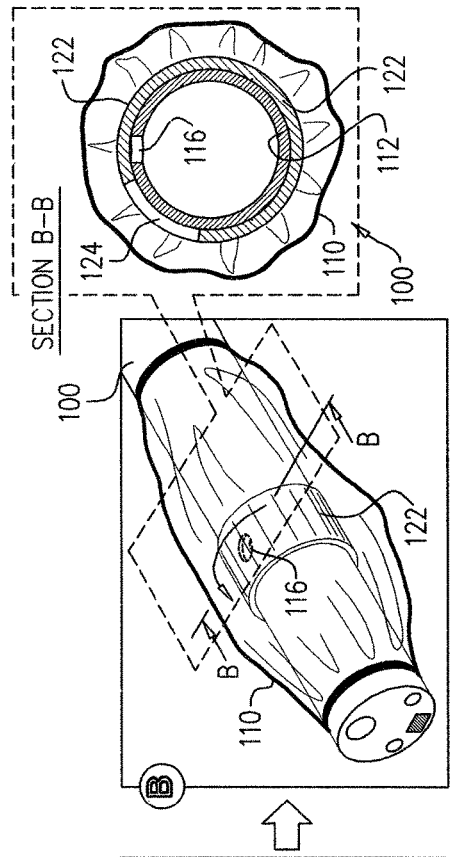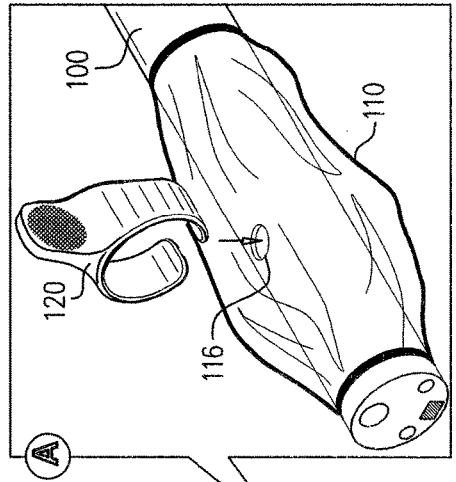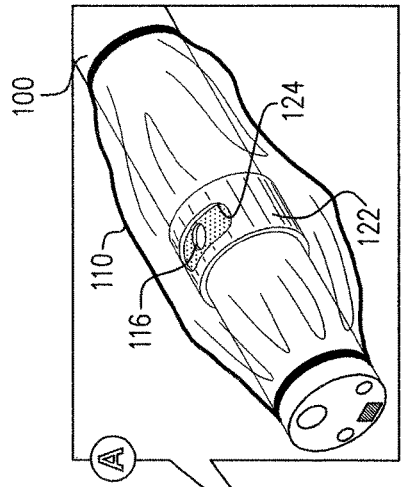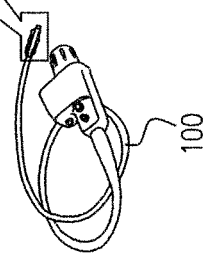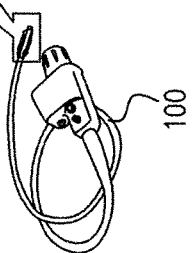
FIG. 1B
FIG. 1C

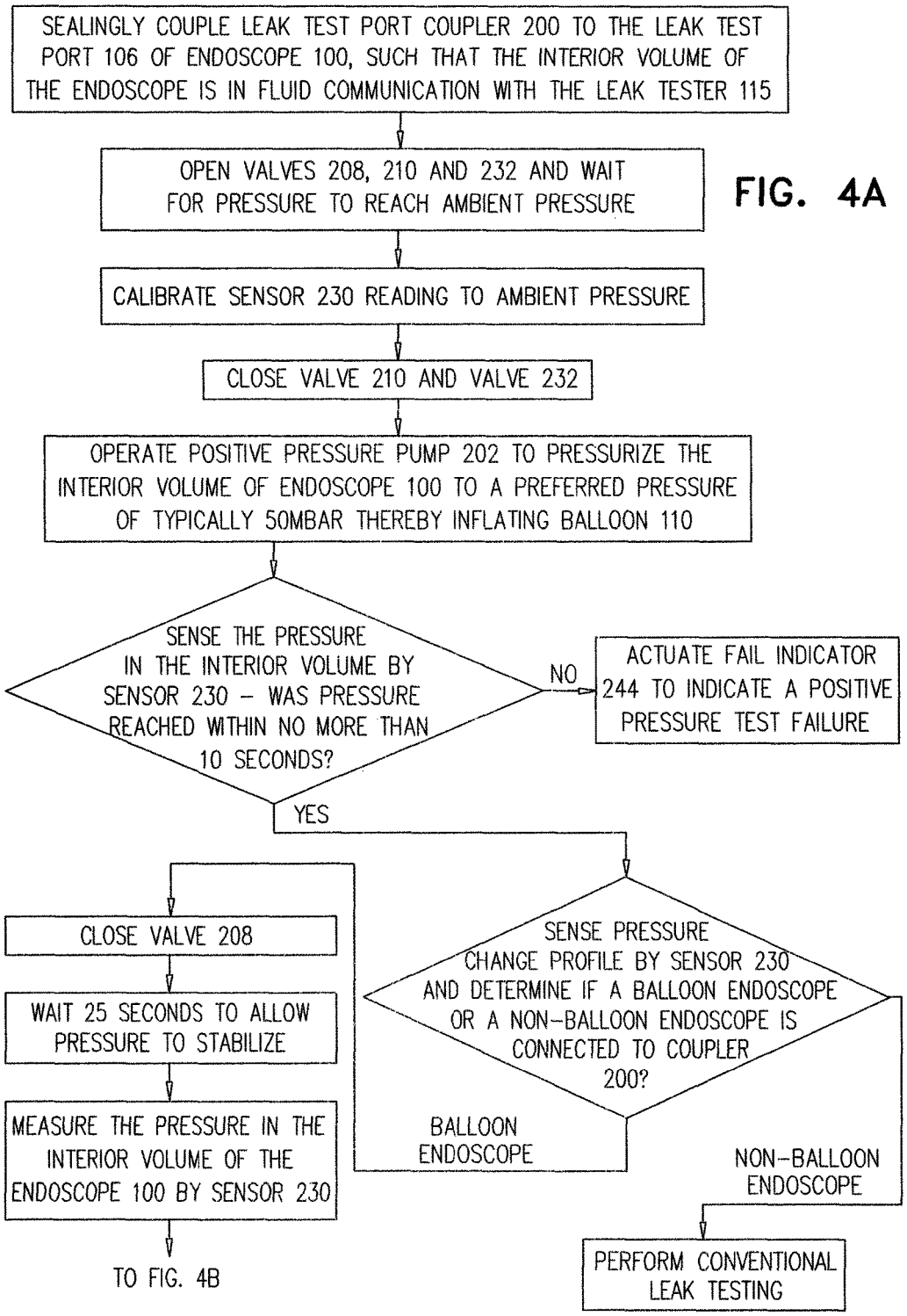

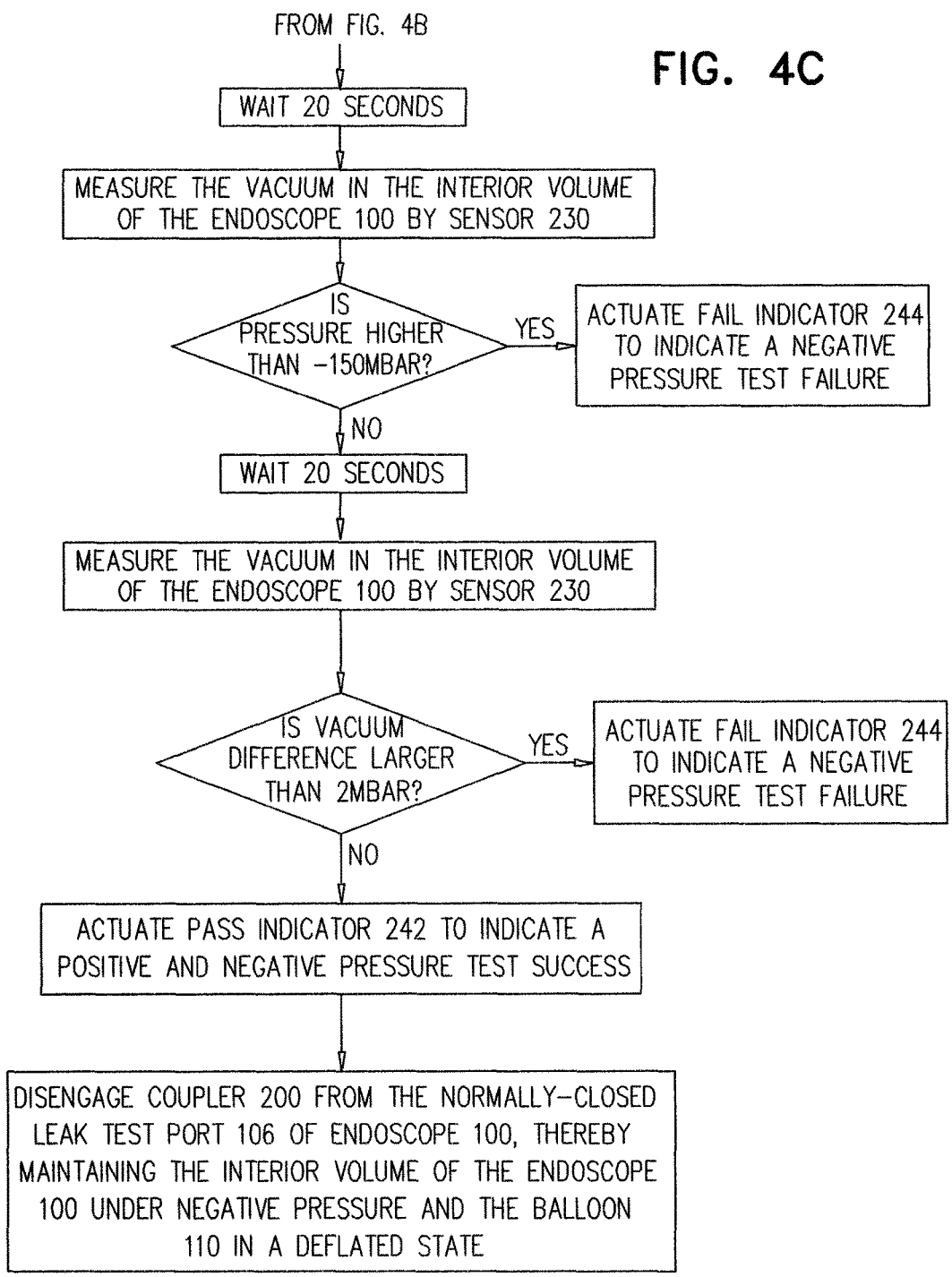

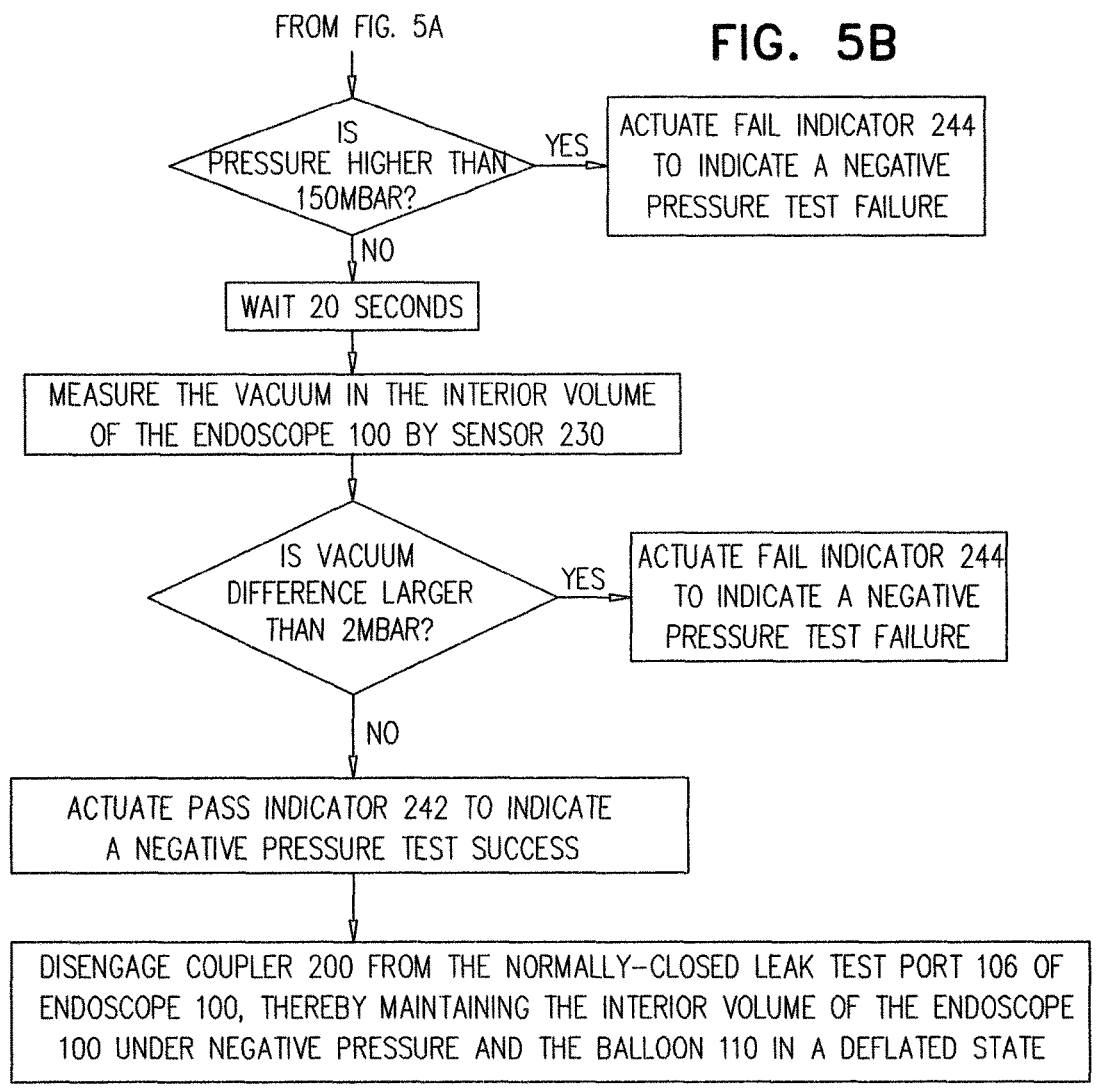

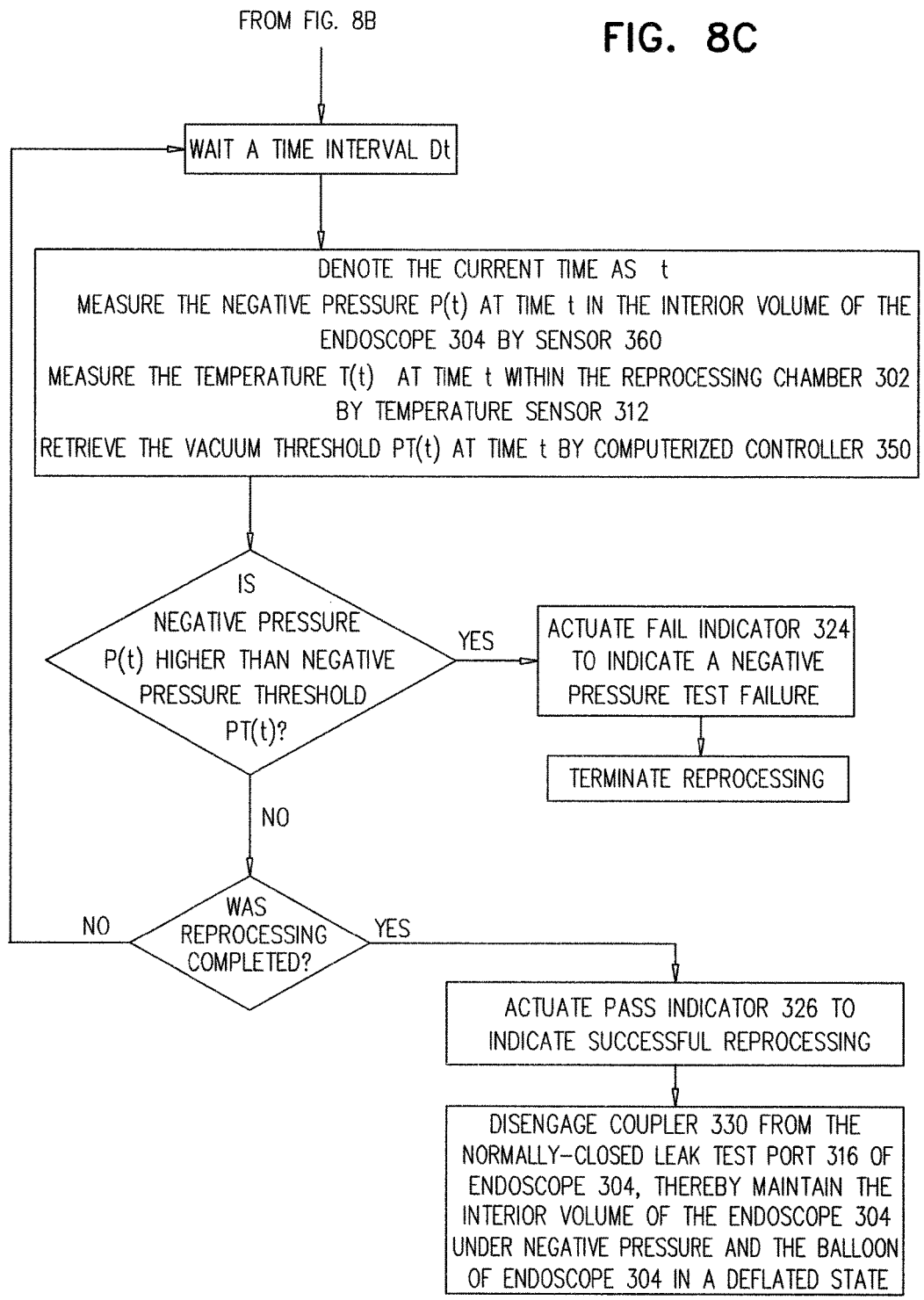

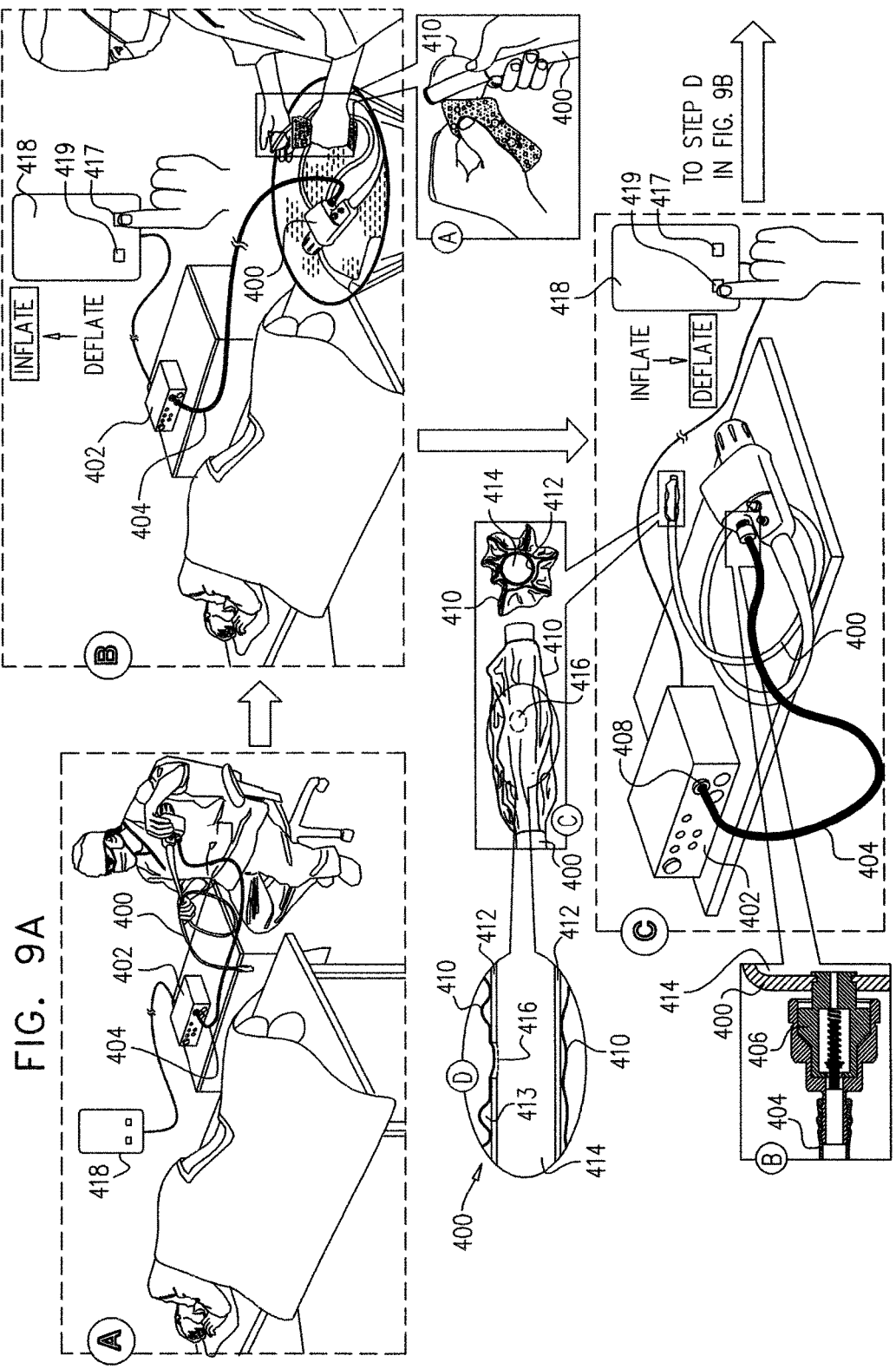

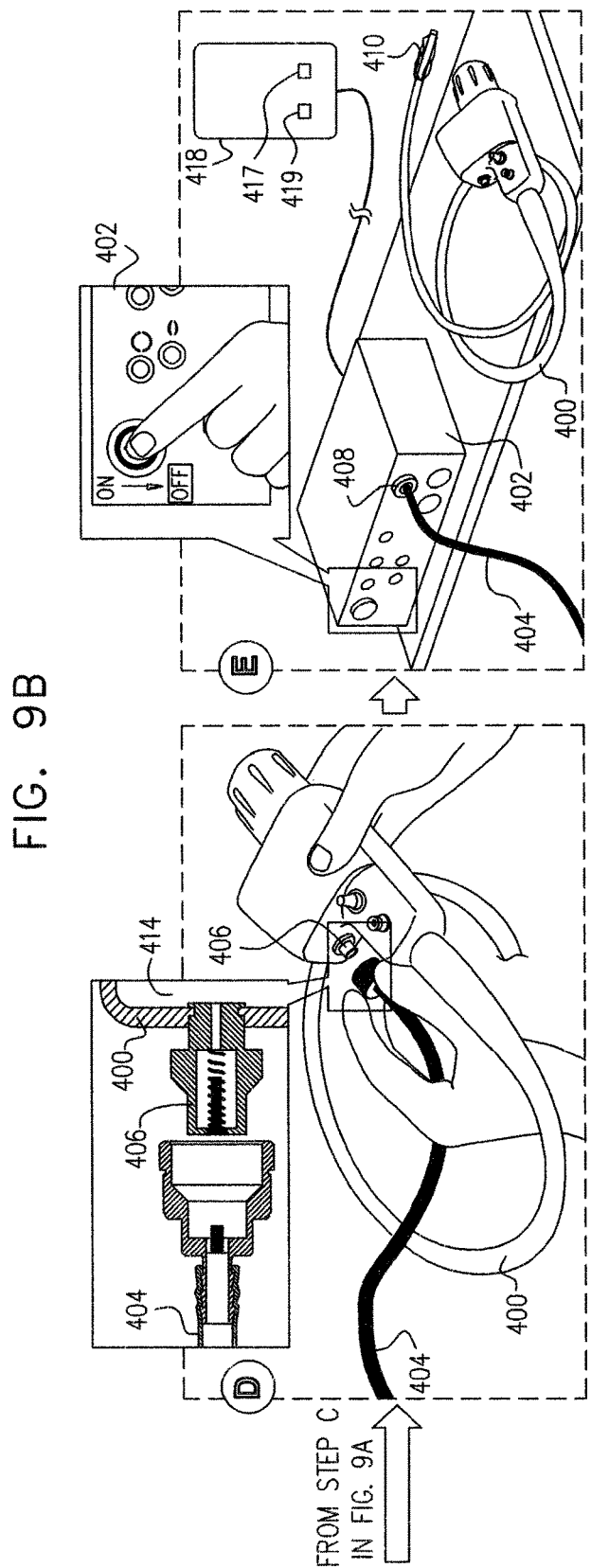

ENDOSCOPE REPROCESSING METHOD

CROSS-REFERENCE TO RELATED APPLICATIONS

This application is a U.S. National Phase Application under 35 U.S.C. 371 of International Application No. PCT/IL2014/000025, which has an international filing date of May 21, 2014, and which claims the benefit of priority of U.S. Provisional Patent Application Ser. No. 61/855,688, filed May 21, 2013 and entitled "ENDOSCOPE REPROCESSING ASSEMBLY AND METHODS" and to U.S. Provisional Patent Application Ser. No. 61/962,383, filed Nov. 6, 2013 and entitled "ENDOSCOPIC REPROCESSING SYSTEM UTILIZING NEGATIVE AIR PRESSURE", the disclosures of which are hereby incorporated by reference and priority of which is hereby claimed pursuant to 37 CFR 1.78(a)(4) and (5)(i).

Reference is also made to the following applicant's Published PCT Patent Applications which are believed to be related to the present application, the contents of which are hereby incorporated by reference herein:
WO2005/0074377; WO2007/017854; WO2007/135665; WO2008/004228; WO2008/142685; WO20099/122395; WO20100/046891; WO2010/137025; WO2011/111040; and WO2014/068569.

FIELD OF THE INVENTION

The present invention relates to endoscope reprocessing systems and methods.

BACKGROUND OF THE INVENTION

Various endoscope reprocessing systems and methods are known.

SUMMARY OF THE INVENTION

The present invention seeks to provide improved endoscope reprocessing methods and systems.

There is thus provided in accordance with a preferred embodiment of the present invention a method for reprocessing a balloon endoscope, the method including the steps of deflating a balloon of a balloon endoscope to a negative pressure state following clinical use thereof and thereafter maintaining the interior of the balloon in a negative pressure state during at least part of reprocessing said balloon endoscope.

Preferably, the reprocessing includes cleaning and the maintaining the interior of the balloon in a negative pressure state during at least part of reprocessing the balloon endoscope includes maintaining the interior of the balloon in a negative pressure state during at least part of the cleaning. Additionally, the cleaning includes at least automated cleaning and the maintaining the interior of the balloon in a negative pressure state during at least part of reprocessing the balloon endoscope includes maintaining the interior of the balloon in a negative pressure state during at least part of the automated cleaning.

In accordance with a preferred embodiment of the present invention the reprocessing includes disinfecting and the maintaining the interior of the balloon in a negative pressure state during at least part of reprocessing the balloon endoscope includes maintaining the interior of the balloon in a negative pressure state during at least part of the disinfecting. Preferably, the cleaning includes at least automated disinfecting and the maintaining the interior of the balloon in a negative pressure state during at least part of reprocessing the balloon endoscope includes maintaining the interior of the balloon in a negative pressure state during at least part of the automated disinfecting.

Preferably, fluid communication exists between the interior of the balloon and an interior volume of the balloon endoscope and the maintaining the interior of the balloon in a negative pressure state during at least part of reprocessing the balloon endoscope includes maintaining the interior volume of the balloon endoscope in a negative pressure state during the at least part of reprocessing.

In accordance with a preferred embodiment of the present invention a normally-closed leak testing port is provided in fluid communication with the balloon endoscope and the maintaining the interior volume of the balloon endoscope in a negative pressure state during the at least part of reprocessing includes deflating the interior volume of the balloon endoscope through the leak testing port. Additionally, the deflating the interior volume of the balloon endoscope through the leak testing port includes coupling a negative pressure device to the leak testing port and operating the negative pressure device to apply vacuum to the interior volume of the endoscope, thereafter, disconnecting the normally-closed leak testing port from the negative pressure pump and maintaining, by the normally-closed leak testing port, negative pressure in the interior volume of the balloon endoscope.

In accordance with a preferred embodiment of the present invention, the deflating a balloon of a balloon endoscope to a negative pressure state includes deflating the balloon to a negative pressure sufficient to maintain deflation of the balloon notwithstanding an increase in temperature encountered during the reprocessing. Preferably, the deflating a balloon of a balloon endoscope to a negative pressure state includes deflating the balloon to a negative pressure in the range of −5 mbar to −300 mbar. More preferably, the deflating a balloon of a balloon endoscope to a negative pressure state includes deflating the balloon to a negative pressure in the range of −100 mbar to −250 mbar. In accordance with a preferred embodiment of the present invention the deflating a balloon of a balloon endoscope to a negative pressure state includes deflating the balloon to a negative pressure below −150 mbar.

Preferably, the deflating a balloon of a balloon endoscope to a negative pressure state includes deflating the balloon to a negative pressure lower than a negative pressure threshold which negative pressure threshold varies over time during reprocessing. Additionally or alternatively, the deflating a balloon of a balloon endoscope to a negative pressure state includes deflating the balloon to a negative pressure lower than a negative pressure threshold which varies as a function of the temperature at the balloon endoscope during the reprocessing. Alternatively or additionally, the deflating a balloon of a balloon endoscope to a negative pressure state includes deflating the balloon to a negative pressure lower than a negative pressure threshold which varies as a function of the measured negative pressure inside the balloon at a specific time prior to or during the reprocessing.

Preferably, the deflating a balloon of a balloon endoscope to a negative pressure state includes deflating the balloon to a negative pressure lower than a negative pressure threshold $PT(t)$ where:

$$PT(t)=F(Tt,T0,P0),$$

where $Tt$ is the temperature at the endoscope at a time $t$, $T0$ is the temperature at the endoscope at an initial time $t0$ and P0 is the pressure at the interior of the balloon of the endoscope at the initial time t0.

In accordance with a preferred embodiment of the present invention the deflating a balloon of a balloon endoscope to a negative pressure state includes deflating the balloon to a negative pressure lower than a negative pressure threshold PT(t) where:

$$PT(t)=F1(Tt,T0,P0)+F2(t-t0)$$

where: Tt is the temperature at the endoscope at a time t, T0 is the temperature at the endoscope at an initial time t0, P0 is the pressure at the interior of the balloon of the endoscope at the initial time t0 and F2 is a function of the elapsed time from time t0 to t.

In accordance with a preferred embodiment of the present invention F1=(Tt/T0)·P0, where Tt and T0 are measured in degrees Kelvin and P0 is measured in the absolute pressure units above zero pressure used for PT(t). Additionally or alternatively, F2=K·(t-t0), where K is a constant, expressing change in pressure over time. Preferably, K is in the range of 0.01-0.20 mbar per second. More preferably, K is in the range of 0.02-0.10 mbar per second.

In accordance with a preferred embodiment of the present invention the method for reprocessing a balloon endoscope also includes the following steps, prior to deflating the balloon to the negative pressure state, inflating the balloon to a positive pressure state following clinical use thereof and cleaning the balloon when it is in the positive pressure state.

There is also provided in accordance with another preferred embodiment of the present invention a balloon endoscope reprocessing system including a balloon endoscope including a balloon having an interior volume and a valve communicating with the interior volume of the balloon, balloon deflation control functionality communicating with the interior volume of the balloon via the valve and being operative to cause the interior volume to be in a negative pressure state and balloon endoscope reprocessing functionality for receiving and at least one of cleaning and disinfecting the balloon endoscope when the interior volume of the balloon is maintained in a negative pressure state.

Preferably, the balloon endoscope reprocessing functionality includes automated endoscope reprocessing functionality.

In accordance with a preferred embodiment of the present invention fluid communication exists between the interior of the balloon and an interior volume of the balloon endoscope and the interior volume of the balloon endoscope is maintained in a negative pressure state during the at least part of reprocessing by the balloon endoscope reprocessing functionality. Additionally, the valve includes a normally-closed leak testing port in fluid communication with the interior volume of the balloon endoscope and the balloon deflation control functionality maintains the interior volume of the balloon endoscope in the negative pressure state during the at least part of reprocessing by deflating the interior volume of the balloon endoscope through the leak testing port.

In accordance with a preferred embodiment of the present invention, the balloon deflation control functionality is operative for deflating the balloon to a negative pressure sufficient to maintain deflation of the balloon notwithstanding an increase in temperature encountered during the reprocessing. Preferably, the balloon deflation control functionality is operative for deflating the balloon to a negative pressure in the range of −5 mbar to −300 mbar. More preferably, the balloon deflation control functionality is operative for deflating the balloon to a negative pressure in the range of −100 mbar to −250 mbar. In accordance with a preferred embodiment of the present invention the balloon deflation control functionality is operative for deflating the balloon to a negative pressure below −150 mbar.

Preferably, the balloon deflation control functionality is operative for deflating the balloon to a negative pressure lower than a negative pressure threshold, which negative pressure threshold varies over time during reprocessing. Additionally or alternatively, the balloon deflation control functionality is operative for deflating the balloon to a negative pressure lower than a negative pressure threshold which varies as a function of the temperature at the balloon endoscope during the reprocessing. Alternatively or additionally, the balloon deflation control functionality is operative for deflating the balloon to a negative pressure lower than a negative pressure threshold which varies as a function of the measured negative pressure inside the balloon at a specific time prior to or during the reprocessing.

In accordance with a preferred embodiment of the present invention the balloon deflation control functionality is operative for deflating the balloon to a negative pressure lower than a negative pressure threshold PT(t) where:

$$PT(t)=F(Tt,T0,P0),$$

where Tt is the temperature at the endoscope at a time t, T0 is the temperature at the endoscope at an initial time t0 and P0 is the pressure at the interior of the balloon of the endoscope at the initial time t0.

In accordance with a preferred embodiment of the present invention the balloon deflation control functionality is operative for deflating the balloon to a negative pressure lower than a negative pressure threshold PT(t) where:

$$PT(t)=F1(Tt,T0,P0)+F2(t-t0)$$

where Tt is the temperature at the endoscope at a time t, T0 is the temperature at the endoscope at an initial time t0, P0 is the pressure at the interior of the balloon of the endoscope at the initial time t0 and F2 is a function of the elapsed time from time t0 to t.

Preferably, F1=(Tt/T0)·P0, where Tt and T0 are measured in degrees Kelvin and P0 is measured in the absolute pressure units above zero pressure used for PT(t). Additionally or alternatively, F2=K·(t-t0), where K is a constant, expressing change in pressure over time. Preferably, K is in the range of 0.01-0.20 mbar per second. More preferably, K is in the range of 0.02-0.10 mbar per second.

There is further provided in accordance with yet another preferred embodiment of the present invention a balloon endoscope reprocessing system including automated balloon endoscope reprocessing functionality for receiving and at least one of cleaning and disinfecting a balloon endoscope and balloon deflation control functionality which is operative to maintain the interior volume of the balloon in a negative pressure state during at least part of operation of the automated balloon endoscope reprocessing functionality.

Preferably, the balloon deflation control functionality is operative to maintain the interior of the balloon in a negative pressure state during all of the operation of the automated balloon endoscope reprocessing functionality.

In accordance with a preferred embodiment of the present invention fluid communication exists between the interior of the balloon and an interior volume of the balloon endoscope and the interior volume of the balloon endoscope is maintained in a negative pressure state during the at least part of reprocessing by the balloon endoscope reprocessing functionality. Additionally, the valve includes a normally-closed leak testing port in fluid communication with the interior volume of the balloon endoscope and the balloon deflation control functionality maintains the interior volume of the balloon endoscope in the negative pressure state during the at least part of reprocessing by deflating the interior volume of the balloon endoscope through the leak testing port.

In accordance with a preferred embodiment of the present invention the balloon deflation control functionality is operative for deflating the balloon to a negative pressure sufficient to maintain deflation of the balloon notwithstanding an increase in temperature encountered during the reprocessing. Preferably, the balloon deflation control functionality is operative for deflating the balloon to a negative pressure in the range of −5 mbar to −300 mbar. More preferably, the balloon deflation control functionality is operative for deflating the balloon to a negative pressure in the range of −100 mbar to −250 mbar. In accordance with a preferred embodiment of the present invention the balloon deflation control functionality is operative for deflating the balloon to a negative pressure below −150 mbar.

In accordance with a preferred embodiment of the present invention the balloon deflation control functionality is operative for deflating the balloon to a negative pressure lower than a negative pressure threshold, which negative pressure threshold varies over time during reprocessing. Additionally or alternatively, the balloon deflation control functionality is operative for deflating the balloon to a negative pressure lower than a negative pressure threshold which varies as a function of the temperature at the balloon endoscope during the reprocessing. Alternatively or additionally, the balloon deflation control functionality is operative for deflating the balloon to a negative pressure lower than a negative pressure threshold which varies as a function of the measured negative pressure inside the balloon at a specific time prior to or during the reprocessing.

In accordance with a preferred embodiment of the present invention the balloon deflation control functionality is operative for deflating the balloon to a negative pressure lower than a negative pressure threshold PT(t) where:

$$PT(t)=F(Tt,T0,P0),$$

where Tt is the temperature at the endoscope at a time t, T0 is the temperature at the endoscope at an initial time t0 and P0 is the pressure at the interior of the balloon of the endoscope at the initial time t0.

In accordance with a preferred embodiment of the present invention the balloon deflation control functionality is operative for deflating the balloon to a negative pressure lower than a negative pressure threshold PT(t) where:

$$PT(t)=F1(Tt,T0,P0)+F2(t-t0)$$

where Tt is the temperature at the endoscope at a time t, T0 is the temperature at the endoscope at an initial time t0, P0 is the pressure at the interior of the balloon of the endoscope at the initial time t0 and F2 is a function of the elapsed time from time t0 to t.

Preferably, $F1=(Tt/T0) \cdot P0$, where Tt and T0 are measured in degrees Kelvin and P0 is measured in the absolute pressure units above zero pressure used for PT(t). Additionally or alternatively, $F2=K \cdot (t-t0)$, where K is a constant, expressing change in pressure over time. Preferably, K is in the range of 0.01-0.20 mbar per second. More preferably, K is in the range of 0.02-0.10 mbar per second.

In accordance with a preferred embodiment of the present invention the balloon endoscope reprocessing system also includes negative pressure leak testing functionality operative to detect leaks in the balloon endoscope under negative pressure during reprocessing.

Preferably, the negative pressure leak testing functionality is configured to be coupled to a leak test port of an endoscope for sensing leaks in the endoscope under negative pressure and includes an indicator operative in response to operation of the negative pressure leak test functionality for indicating the presence or absence of a leak in the endoscope. Additionally or alternatively, the negative pressure leak testing functionality is operative to sense leaks at multiple times during the reprocessing. In accordance with a preferred embodiment of the present invention the multiple times occur periodically. Alternatively, the multiple times occur immediately one after the other.

In accordance with a preferred embodiment of the present invention the balloon endoscope reprocessing system also includes non-balloon endoscope reprocessing functionality.

Preferably, the balloon endoscope reprocessing system also includes an operator selection interface allowing an operator to select functionality suitable for reprocessing of a balloon endoscope or functionality suitable for reprocessing of a non-balloon endoscope.

In accordance with a preferred embodiment of the present invention the negative pressure leak test functionality is operative to perform leak testing when the interior volume of the endoscope is at a negative pressure which is different from a negative pressure of the interior volume of the endoscope during reprocessing when leak testing is not taking place. Additionally, the negative pressure of the interior volume of the endoscope during the leak testing is at a stronger vacuum than the negative pressure of the interior volume of the endoscope during reprocessing when leak testing is not taking place.

There is even further provided in accordance with still another preferred embodiment of the present invention a leak testing device for use with an endoscope having a leak test port, the leak testing device including negative pressure leak test functionality configured to be coupled to a leak test port of an endoscope for sensing leaks in the endoscope under negative pressure and an indicator operative in response to operation of the negative pressure leak test functionality for indicating the presence or absence of a leak in the endoscope.

Preferably, the negative pressure leak test functionality is operative for performing the leak testing when the negative pressure is in the range of −5 mbar to −300 mbar. More preferably, the negative pressure leak test functionality is operative for performing the leak testing when the negative pressure is in the range of −100 mbar to −250 mbar. In accordance with a preferred embodiment of the present invention the negative pressure leak test functionality is operative for performing the leak testing when the negative pressure is below −150 mbar.

In accordance with a preferred embodiment of the present invention the leak testing device for use with an endoscope is suitable for use in conjunction with reprocessing of a balloon endoscope having an interior volume and the device also includes negative pressure establishment functionality operative subsequent to at least one leak test to establish a negative pressure in the interior volume of the balloon endoscope which is suitable for reprocessing of the balloon endoscope.

Preferably, the leak testing device for use with an endoscope also includes positive pressure leak testing functionality. Additionally, the positive pressure leak testing functionality includes functionality for eliminating false leak indications resulting from expansion of an endoscope balloon over time during leak testing.

In accordance with a preferred embodiment of the present invention the leak testing device for use with an endoscope also includes automatic balloon endoscope/non-balloon endoscope sensing functionality. Additionally, the leak testing device for use with an endoscope also includes a computerized controller for operating the leak testing device differently depending on whether it is connected to a balloon endoscope or a non-balloon endoscope.

There is still further provided in accordance with another preferred embodiment of the present invention a leak testing method for use with an endoscope having a leak test port, the method including coupling negative pressure leak test functionality to an interior volume of an endoscope, employing the negative pressure leak test functionality for sensing leaks in the endoscope under negative pressure and in response to operation of the negative pressure leak test functionality, indicating the presence or absence of a leak in the endoscope.

Preferably, the negative pressure leak test functionality is operative for performing the leak testing when the negative pressure is in the range of −5 mbar to −300 mbar. More preferably, the negative pressure leak test functionality is operative for performing the leak testing when the negative pressure is in the range of −100 mbar to −250 mbar. In accordance with a preferred embodiment of the present invention the negative pressure leak test functionality is operative for performing the leak testing when the negative pressure is below −150 mbar.

In accordance with a preferred embodiment of the present invention the leak testing method, for use with an endoscope which is suitable for use in conjunction with reprocessing of a balloon endoscope having an interior volume, also includes, subsequent to performing at least one leak test, establishing a negative pressure in the interior volume of the balloon endoscope which negative pressure is suitable for reprocessing of the balloon endoscope.

Preferably, the leak testing method for use with an endoscope also includes positive pressure leak testing. Additionally, the positive pressure leak testing includes eliminating false leak indications resulting from expansion of an endoscope balloon over time during leak testing.

In accordance with a preferred embodiment of the present invention the leak testing method for use with an endoscope also includes automatic sensing of a connection to either a balloon endoscope or a non-balloon endoscope. Additionally, the leak testing method for use with an endoscope also includes operating the leak testing device differently depending on whether it is connected to a balloon endoscope or a non-balloon endoscope.

There is also provided in accordance with yet another preferred embodiment of the present invention an endoscope reprocessing system having dual mode leak test port connection functionality which has a first, non-balloon endoscope, reprocessing mode in which pressurized gas is supplied to a leak test port of a non-balloon endoscope undergoing reprocessing and a second, balloon endoscope, reprocessing mode in which pressurized gas is not supplied to a leak test port of a balloon endoscope.

There is even further provided in accordance with still another preferred embodiment of the present invention a retrofit automated balloon endoscope reprocessing system for use with a conventional automated reprocessing machine, having a source of pressurized gas, which conventional automated reprocessing machine is not suitable for reprocessing balloon endoscopes, the retrofit system including a pre-reprocessing balloon endoscope balloon deflation verifier and a balloon endoscope reprocessing enabler, allowing normal operation of the conventional automated reprocessing machine while the leak test port of the balloon endoscope is not in pressurized gas communication with a source of pressurized gas.

There is yet further provided in accordance with even yet another preferred embodiment of the present invention a retrofit automated balloon endoscope reprocessing system for use with a conventional automated reprocessing machine, having a source of pressurized gas, which conventional automated reprocessing machine is not suitable for reprocessing balloon endoscopes, the retrofit system including a pre-reprocessing balloon endoscope balloon deflation verifier and a reprocessing balloon endoscope leak test port inflation preventer operative to prevent inflation of a balloon of a balloon endoscope via its leak test port while allowing otherwise normal operation of the conventional automated reprocessing machine.

There is still further provided in accordance with another preferred embodiment of the present invention an endoscope leak test device including a leak test port coupler, a computerized negative pressure applier configured to apply negative pressure to a leak test port of an endoscope via the leak test port coupler and a computerized pressure sensor configured to sense changes in pressure over time at the leak test port of the endoscope at a time when the leak test port is under negative pressure.

There is also provided in accordance with yet another preferred embodiment of the present invention an endoscope leak test device including a leak test port coupler, a computerized pressure applier configured to apply, at different times, positive pressure and negative pressure to a leak test port of an endoscope via the leak test port coupler and a computerized pressure sensor configured to sense changes in pressure over time at the leak test port of the endoscope both at a time when the leak test port is under positive pressure and at a time when the leak test port is under negative pressure.

There is further provided in accordance with still another preferred embodiment of the present invention an endoscope leak test device including a positive pressure source, a negative pressure source, a computerized pressure controller configured to apply, at different times, positive pressure from the positive pressure source and negative pressure from the negative pressure source to a leak test port of an endoscope and a computerized pressure sensor configured to sense changes in pressure over time at the leak test port of the endoscope both at a time when the leak test port is under positive pressure and at a time when the leak test port is under negative pressure.

There is still further provided in accordance with yet another preferred embodiment of the present invention an automated endoscope reprocessor including an endoscope reprocessing chamber which is configured for receiving an endoscope to be reprocessed, a fluid supply subsystem operative to provide a flow of reprocessing materials to the endoscope reprocessing chamber and a leak testing subsystem which is configured for connection to a leak test port of the endoscope to be reprocessed, the leak testing subsystem having negative pressure leak testing functionality for providing negative pressure leak testing of the endoscope.

Preferably, the automated endoscope reprocessor also includes a computerized controller coordinating the relative timing of operation of the fluid supply subsystem and the leak testing subsystem.

In accordance with a preferred embodiment of the present invention the fluid supply subsystem provides fluid at an elevated temperature to the endoscope reprocessing chamber during at least one phase of operation of the reprocessor and the computerized controller ensures that an interior volume of the endoscope is at least at a predetermined negative pressure during the at least one phase of operation of the reprocessor. Additionally, the computerized controller is operative to selectably govern the operation of the fluid supply system and the leak testing subsystem in a balloon endoscope reprocessing mode and in a non-balloon endoscope processing mode. Preferably, the computerized controller is operative in the balloon endoscope reprocessing mode to perform leak testing only while the balloon endoscope is in a depressurized state such that a balloon thereof is in a deflated state. Additionally or alternatively, the computerized controller is operative in the balloon endoscope reprocessing mode to perform reprocessing only while the balloon endoscope is in a depressurized state such that a balloon thereof is in a deflated state.

There is yet further provided in accordance with still another preferred embodiment of the present invention a method for reprocessing a balloon endoscope, having an endoscope interior volume, and including a balloon, having a balloon interior volume, the endoscope interior volume and the balloon interior volume being normally in fluid communication via at least one aperture, the method including sealing the at least one aperture during at least part of reprocessing of the balloon endoscope.

Preferably, the sealing is effected by mechanically sealing the at least one aperture. Additionally, the sealing is effected by application of vacuum to the endoscope interior volume which tightly holds the balloon in sealing engagement with the at least one aperture. Preferably, the balloon is mounted over an outer sheath of the balloon endoscope and the sealing is effected by application of an external clip which is operative to press the balloon against the outer sheath, circumferentially around the at least one aperture, thereby sealing the at least one aperture. More preferably, the sealing is effected by application of a mechanical sealing element which is operative to block the at least one aperture, thereby sealing the at least one aperture and preventing flow of fluids therethrough. Yet preferably, the mechanical sealing element is placed interiorly of the balloon.

There is yet further provided in accordance with still another preferred embodiment of the present invention a balloon endoscope having an endoscope interior volume and including a balloon which is sealingly mounted over an outer sheath of the balloon endoscope and having a balloon interior volume, at least one aperture disposed in the outer sheath underneath the balloon and normally providing fluid communication between the endoscope interior volume and the balloon interior volume, and a sealing element operative for sealing the at least one aperture during at least part of reprocessing of the balloon endoscope. Preferably, the sealing element includes an external clip which is operative to press the balloon against the outer sheath, circumferentially around the at least one aperture, thereby sealing the at least one aperture. Alternatively, the sealing element includes a mechanical sealing element which is operative to block the at least one aperture, thereby sealing the at least one aperture and preventing flow of fluids therethrough. Preferably, the mechanical sealing element is placed interiorly of said balloon.

There is even further provided in accordance another preferred embodiment of the present invention a method for preparing a balloon endoscope for reuse, the method including the steps of inflating a balloon of a balloon endoscope to a positive pressure state following clinical use thereof, cleaning the balloon when it is in the positive pressure state, thereafter deflating the balloon of a balloon endoscope to a negative pressure state and thereafter reprocessing the balloon endoscope while maintaining the interior of the balloon in a negative pressure state during at least part of reprocessing the balloon endoscope.

BRIEF DESCRIPTION OF THE DRAWINGS

The present invention will be understood and appreciated more fully from the following detailed description, taken in conjunction with the drawings in which:

FIGS. 1A, 1B, 1C and 1D are simplified illustrations of a reprocessing method operative in accordance with a preferred embodiment of the present invention;

FIGS. 4A, 4B and 4C are together a simplified flow chart of the operation of the leak tester of FIG. 3 in accordance with one embodiment of the present invention;

FIGS. 5A and 5B are together a simplified flow chart of the operation of the leak tester of FIG. 3 in accordance with another embodiment of the present invention;

FIGS. 8A, 8B and 8C are together a simplified flow chart of the operation of the reprocessing system of FIG. 6 in accordance with another embodiment of the present invention; and FIGS. 9A and 9B are simplified illustrations of a reprocessing method operative in accordance with a preferred embodiment of the present invention.

DETAILED DESCRIPTION OF PREFERRED EMBODIMENTS

Unless specifically indicated herein to the contrary, negative pressure, or vacuum, is defined hereinbelow as a pressure lower than ambient, typically atmospheric, pressure. Accordingly, a decrease in vacuum means an increase in the absolute pressure, which remains lower than ambient pressure. More specifically, a higher negative pressure means a weaker vacuum, and a negative pressure lower than a given pressure threshold means a pressure which is lower in its absolute value (above zero pressure) than that given pressure threshold.

Figure 1D:
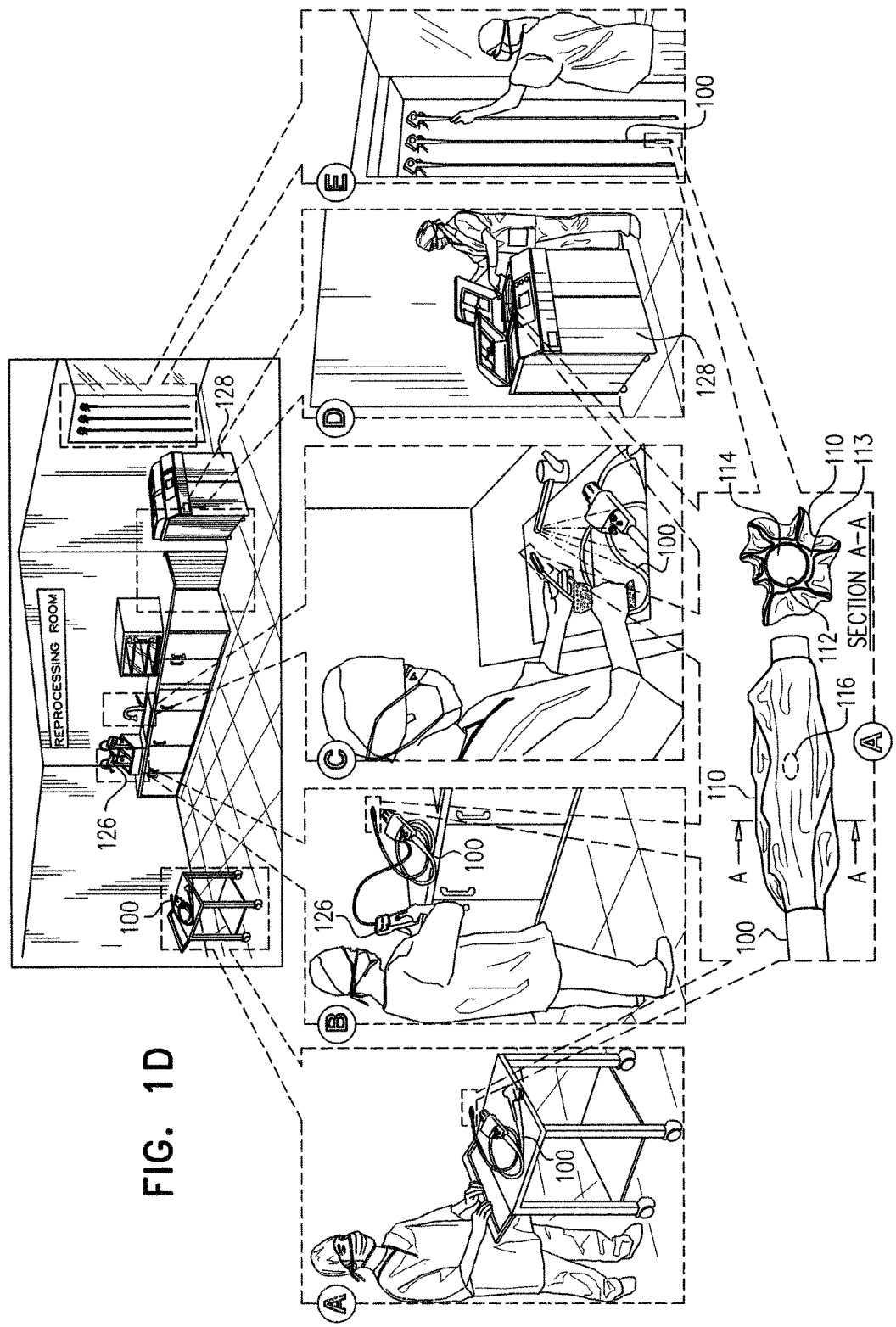
Figure 2:
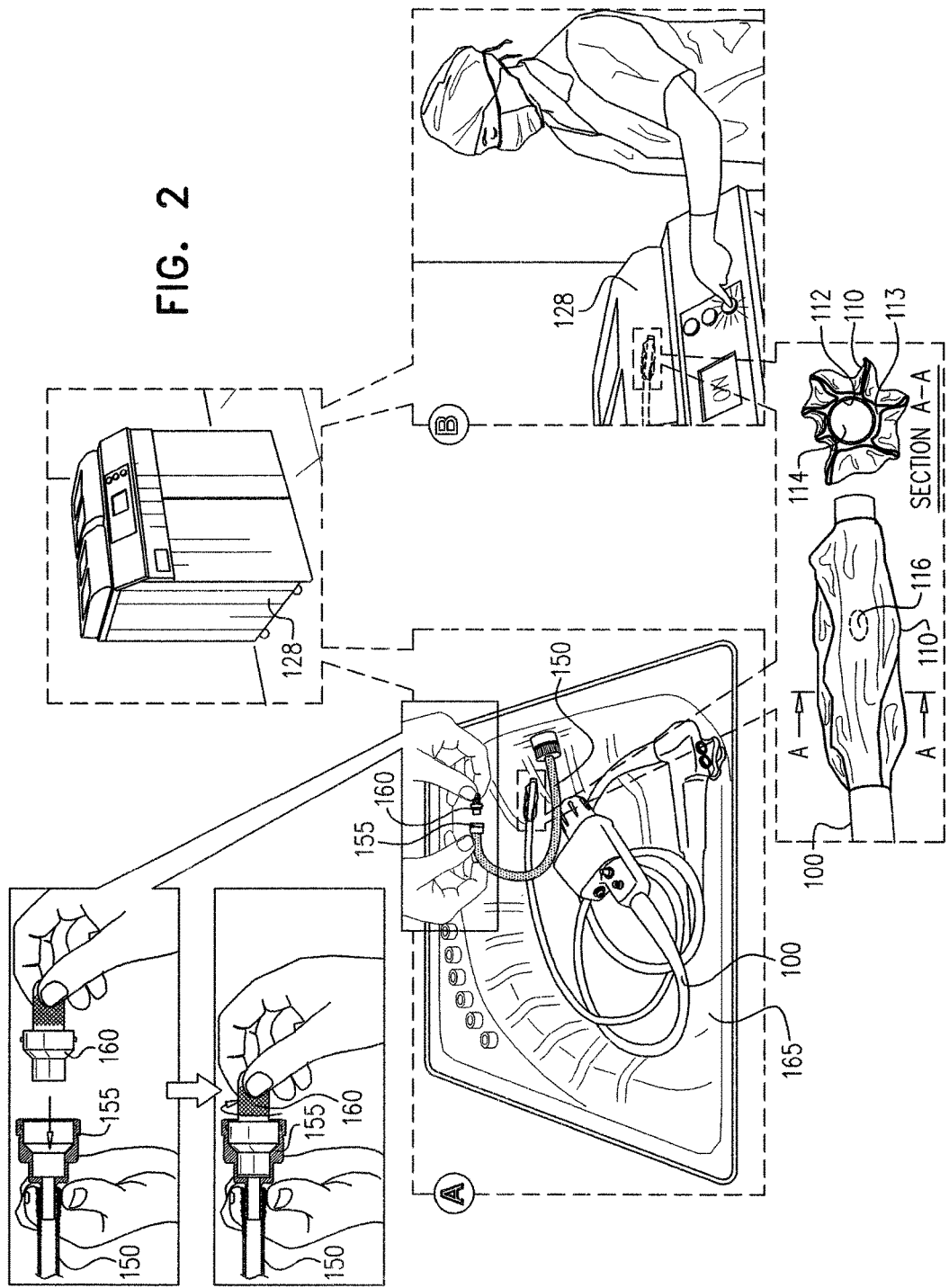
FIG. 2 is a simplified illustration of details of one of the steps shown in FIG. 1B.

Reference is now made to FIGS. 1A-1D, which are simplified illustrations of a reprocessing method operative in accordance with a preferred embodiment of the present invention and to FIG. 2, which is a simplified illustration of details of one of the steps shown in FIG. 1D.

As seen in FIGS. 1A-2, there is provided a reprocessing method for a balloon endoscope, which is particularly characterized in that it includes:

deflating a balloon of a balloon endoscope to a negative pressure state following clinical use thereof; and thereafter maintaining the interior of the balloon in a negative pressure state during at least part of reprocessing said balloon endoscope.

There is also provided a method for reprocessing a balloon endoscope having a balloon interior volume and an endoscope interior volume which are normally in fluid communication via at least one aperture, the method comprising sealing the at least one aperture during at least part of reprocessing of the balloon endoscope.

FIG. 1A, illustrates steps carried out in an endoscopy room. Step A, shown in FIG. 1A, illustrates a balloon endoscope 100, such as a model G-EYE™ 3890i colonoscope, commercially available from Smart Medical Systems of 10 Hayetsira street, Raanana 43663, Israel, after having been removed from the body of a patient following an endoscopic procedure, such as a colonoscopy. At this stage, the balloon of the balloon endoscope 100 may be inflated or deflated.

During the endoscopic procedure and immediately thereafter at Steps A and B, the balloon endoscope 100 is operatively connected with an inflation/deflation system 102, such as a SPARK2C inflation system, commercially available from Smart Medical Systems of Raanana, Israel. Specifically a flexible inflation/deflation tube 104 is sealingly connected at one end thereof to a normally-closed leak-test port 106 of balloon endoscope 100, as seen in enlargement A, and is sealingly connected at an opposite end thereof to an inflation/deflation tube connection port 108 of the inflation/deflation system 102.

As further seen in FIG. 1A, balloon endoscope 100 includes a balloon 110 at its forward portion, which is sealingly mounted over an outer sheath 112 of balloon endoscope 100. An interior volume 113 of balloon 110 is normally in fluid communication with an interior volume 114 of balloon endoscope 100, via at least one aperture 116 formed in the outer sheath 112 of the endoscope 100. It is thus appreciated that balloon 110 may be inflated and deflated by inflation/deflation system 102 via flexible inflation/deflation tube 104, leak test port 106, interior volume 114 of balloon endoscope 100, and at least one aperture 116, altogether forming a continuous fluid communication path between inflation/deflation system 102 and the interior volume 113 of balloon 110.

It is appreciated that the volume of balloon endoscope 100 interiorly of outer sheath 112 may contain various conduits and channels passing therethrough (not shown), such as optical and illumination bundles, electronics, steering wires, instrument channel, and other components as appropriate. It is appreciated that inflation/deflation air can flow freely through the interior volume 114, which is the volume interior to outer sheath 112 that is not occupied by such conduits and channels.

In step B, shown in FIG. 1A, it is seen that if the balloon 110 of the endoscope 100 is not already fully deflated, as seen in enlargement B, the operator presses on a deflate control button 117 of an inflation/deflation control unit 118 of the inflation/deflation system 102 to cause the inflation/deflation system 102 to fully deflate the balloon 110.

It is a particular feature of an embodiment of the present invention that deflation of the balloon 110 effects sealing, as shown in enlargement C, during at least part of reprocessing of the balloon endoscope, of the at least one aperture 116 formed in the outer sheath 112 of the endoscope 100, which aperture normally provides fluid communication between the interior volume 113 of balloon 110 and the interior volume 114 of the endoscope 100. This is important in order to ensure that any reprocessing fluids that might somehow enter the interior volume 113 of balloon 110 from the outside during reprocessing do not enter the interior volume 114 of the endoscope.

It is appreciated that such sealing, during at least part of reprocessing of the balloon endoscope, of the at least one aperture 116, could be provided otherwise than by means of deflation of the balloon 110, such as by a mechanical sealing element or shutter that blocks the at least one aperture 116 and prevents flow of fluids therethrough. It is further appreciated that such a mechanical sealing element or shutter may be placed either exteriorly or interiorly of outer sheath 112 and/or balloon 110.

FIG. 1B shows mechanical sealing of aperture 116 by an external clip 120, which is operative to press balloon 110 against the outer sheath 112, around the at least one aperture 116, thereby sealing the at least one aperture 116 and blocking flow of fluids therethrough. Step A in FIG. 1B shows the external clip 120 prior to operative engagement with balloon 110 and outer sheath 112, and step B in FIG. 1B shows the clip 120 in pressing operative engagement with balloon 110 and outer sheath 112 around the aperture 116, thereby sealing it.

FIG. 1C shows mechanical sealing of the at least one aperture 116 by a mechanical shutter 122, forming part of endoscope 100 and located in proximity to the at least one aperture 116 and interiorly of balloon 110. In the example of FIG. 1C, mechanical shutter 122 is formed of a circular band encircling outer sheath 112 around and over the at least one aperture 116, having an oval shutter aperture 124 formed therein. Preferably, the dimensions of shutter aperture 124 are larger than that of the at least one aperture 116.

At step A shown in FIG. 1C, mechanical shutter 122 assumes a non-sealing orientation, wherein shutter aperture 124 is positioned over aperture 116, thereby allowing flow of fluids through aperture 116, as applicable in the clinical use of endoscope 100. Step B in FIG. 1C shows the mechanical shutter 122 being rotated counter-clockwise, such as by an operator manually rotating it through the flexible balloon 110, so as to radially mis-align shutter aperture 124 with respect to aperture 116, and seal aperture 116 by shutter 122.

Returning now to FIG. 1A, at step C the operator disconnects the flexible inflation/deflation tube 104 from normally-closed leak-test port 106 of balloon endoscope 100. Due to the normally-closed operation of leak-test port 106, interior volume 114 of endoscope 100 remains in a vacuum state and the balloon 110 remains fully deflated.

Step D of FIG. 1A, shows subsequent shut-down of the inflation/deflation system 102.

It is a particular feature of the embodiment of the present invention described with reference to FIG. 1A that balloon endoscope 100, while balloon 110 is in a deflated state, is disconnected from inflation/deflation system 102 while the inflation/deflation system 102 is powered on and thereby maintaining vacuum in interior volume 114 of endoscope 100 and deflation of balloon 110, and that system 102 is powered off only after its disconnection from endoscope 100.

FIG. 1D shows subsequent steps which take place in a reprocessing room of a medical facility, which is separate from and typically adjacent to the endoscopy room. Step A shown in FIG. 1D, shows balloon endoscope 100 being brought into the reprocessing room, it being noted that at this stage the balloon 110 is in a fully deflated state, as seen in enlargement A.

Step B, shown in FIG. 1D, shows an optional leak testing procedure which is carried out preferably using a leak tester 126 of the type described hereinbelow with reference to FIGS. 3-5B.

Step C, shown in FIG. 1D, shows an optional manual reprocessing procedure wherein the balloon endoscope 100 is cleaned and disinfected by hand, preferably according to the procedure set forth in the Instructions For Use (IFU) document provided with balloon endoscope model G-EYE™ 3890i colonoscope, commercially available from Smart Medical Systems of Raanana, Israel, it being noted that reprocessing takes place while balloon 110 is in a fully deflated state, as seen in enlargement A.

Step D, shown in FIG. 1D, shows an alternative or additional automated reprocessing procedure, typically employing an automated reprocessing machine 128 such as a Model WASSENBURG® WD440 Endoscope Washer Disinfector, commercially available from Wassenburg Medical Devices B.V. of Edisonring 9, 6669 NA, Dodewaard, the Netherlands. It is appreciated that if Step C is employed, step D may be obviated and vice versa, although both steps may also be employed. It is noted that reprocessing takes place while balloon 110 is in a fully deflated state, as seen in enlargement A.

Step E, shown in FIG. 1D, shows storage of reprocessed balloon endoscopes 100, it being noted that they are preferably stored with their balloons 110 in a fully deflated state, as seen in enlargement A.

Reference is now made to FIG. 2, which is a simplified illustration of details of one of the steps shown in FIG. 1D. As seen in FIG. 2, an automated reprocessing machine 128, such as Model WASSENBURG® WD440 Endoscope Washer Disinfector, commercially available from Wassenburg Medical Devices B.V. of Edisonring 9, 6669 NA, Dodewaard, the Netherlands, is employed. Automated reprocessing machine 128 typically includes a tube 150, which is, in the prior art, connected to a leak test port of a non-balloon endoscope via a leak test port connector 155. During conventional reprocessing of a non-balloon endoscope by the conventional automated reprocessing machine 128, the interior volume of the non-balloon endoscope may be pressurized through tube 150, for monitoring and detecting potential leaks in the non-balloon endoscope.

In accordance with a preferred embodiment of the present invention, conventional automated reprocessing machines 128 can be employed for reprocessing of balloon endoscopes 100 while balloon 110 is deflated and the interior volume of balloon-endoscope 100 is in vacuum state, preferably by attaching a sealing plug 160 to the leak test port connector 155 at the corresponding end of tube 150, thereby sealing tube 150.

It is appreciated that were tube 150 connected to the leak-test port of endoscope 100, this would result in rupture of balloon 110 due to inflation of the balloon 110 during reprocessing. Were tube 150 left unconnected, this would be perceived by automated reprocessing machine 128 as a leak in the reprocessed endoscope, and would result in a malfunction indication, preventing operation of the automated reprocessing machine 128.

Step A in FIG. 2 shows the balloon endoscope 100 being placed in a reprocessing chamber 165 of the conventional reprocessing machine 128, and the sealing plug 160 being inserted to the leak test port connector 155 of tube 150, thereby sealing tube 150 and providing a retrofitted reprocessing system which can reprocess balloon endoscope 100 in a conventional manner, while balloon 110 is deflated, as seen at step B in FIG. 2.

It is appreciated that in the embodiment of FIGS. 1A-2, leak tester 126 functions as a pre-reprocessing balloon endoscope balloon deflation verifier, which ensures deflation of balloon 110 of balloon endoscope 100 prior to reprocessing, and sealing plug 160 functions as a balloon endoscope reprocessing enabler, allowing normal operation of the conventional automated reprocessing machine 128 while the leak test port 106 of balloon endoscope 100 is not in pressurized gas communication with a source of pressurized gas of conventional automated reprocessing machine 128.

Figure 3:
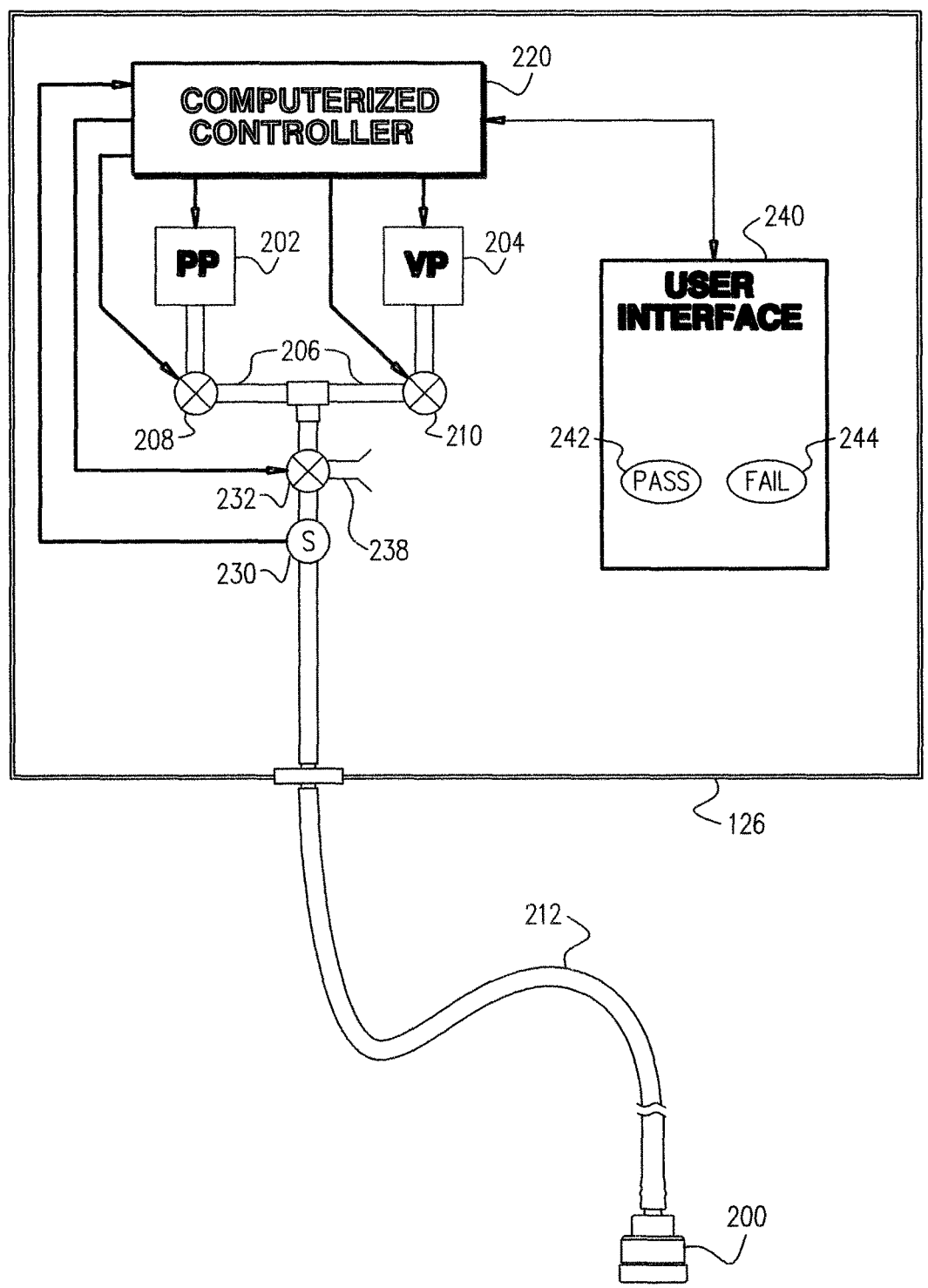
FIG. 3 is a simplified block diagram illustration of a leak tester useful in an embodiment of the reprocessing method of FIGS. 1A & 1B.

Reference is now made to FIG. 3, which is a simplified block diagram illustration of a leak tester 126 useful in an embodiment of the reprocessing method of FIGS. 1A-1D.

As seen in FIG. 3, the leak tester comprises a leak test port coupler 200, which is adapted to connect with a leak test port of a conventional non-balloon endoscope or a conventional balloon endoscope.

A positive gas pressure source, such as an air pump 202 and a negative gas pressure source, such as a vacuum pump 204 are preferably connected to leak test port coupler 200 via a manifold 206 and automatically controllable valves 208 and 210 and a flexible tube 212. A computerized controller 220 is operative to control the operation of pumps 202 and 204 and/or valves 208 and 210 in order to apply at different times, positive pressure and negative pressure to the leak test port of an endoscope via the leak test port coupler 200. Alternatively, a single pump providing at different times, positive and negative pressure may be employed. An example of such a pump is a model 250 EC, commercially available from Schwarzer Precision GmbH+Co. KG of Am Lichtbogen 7, 45141 Essen, Germany.

A computerized pressure sensor 230 is preferably coupled to leak test port coupler 200 and may also be coupled to pumps 202 and 204 via a valve 232 and is configured to sense changes in pressure over time at the leak test port of the endoscope both at a time when the leak test port is under positive pressure and at a time when the leak test port is under negative pressure.

Preferably, each of valves 208 and 210 is an automatically controllable valve having two states—an "open" state in which the valve allows gas flow between the corresponding pump and the manifold 206, and a "closed" state in which the valve blocks gas flow between the pump and the manifold 206.

Preferably, valve 232 is an automatically controllable two-state valve, which can be positioned in either an "open" state in which it connects tube 212 and manifold 206 to the ambient via a purge tube 238, and a "closed" state in which it connects manifold 206 and tube 212 to each other while disconnecting them from purge tube 238 and preventing air communication with the ambient.

In accordance with a preferred embodiment of the present invention, the computerized controller 220 cooperates with the computerized pressure sensor 230 to carry out a positive and negative pressure leak test protocol, two preferred embodiments of which are set forth in FIGS. 4A-4C and 5A-5B.

A user interface 240 is preferably provided integrally with the leak tester 126 and preferably includes first and second visible indicators 242 and 244, which respectively indicate test PASS or FAIL.

It is appreciated that in accordance with another preferred embodiment of the invention, only a negative pressure leak test is performed and in such a case, the positive pressure pump 202 and its associated connections may be obviated.

Figure 4B:
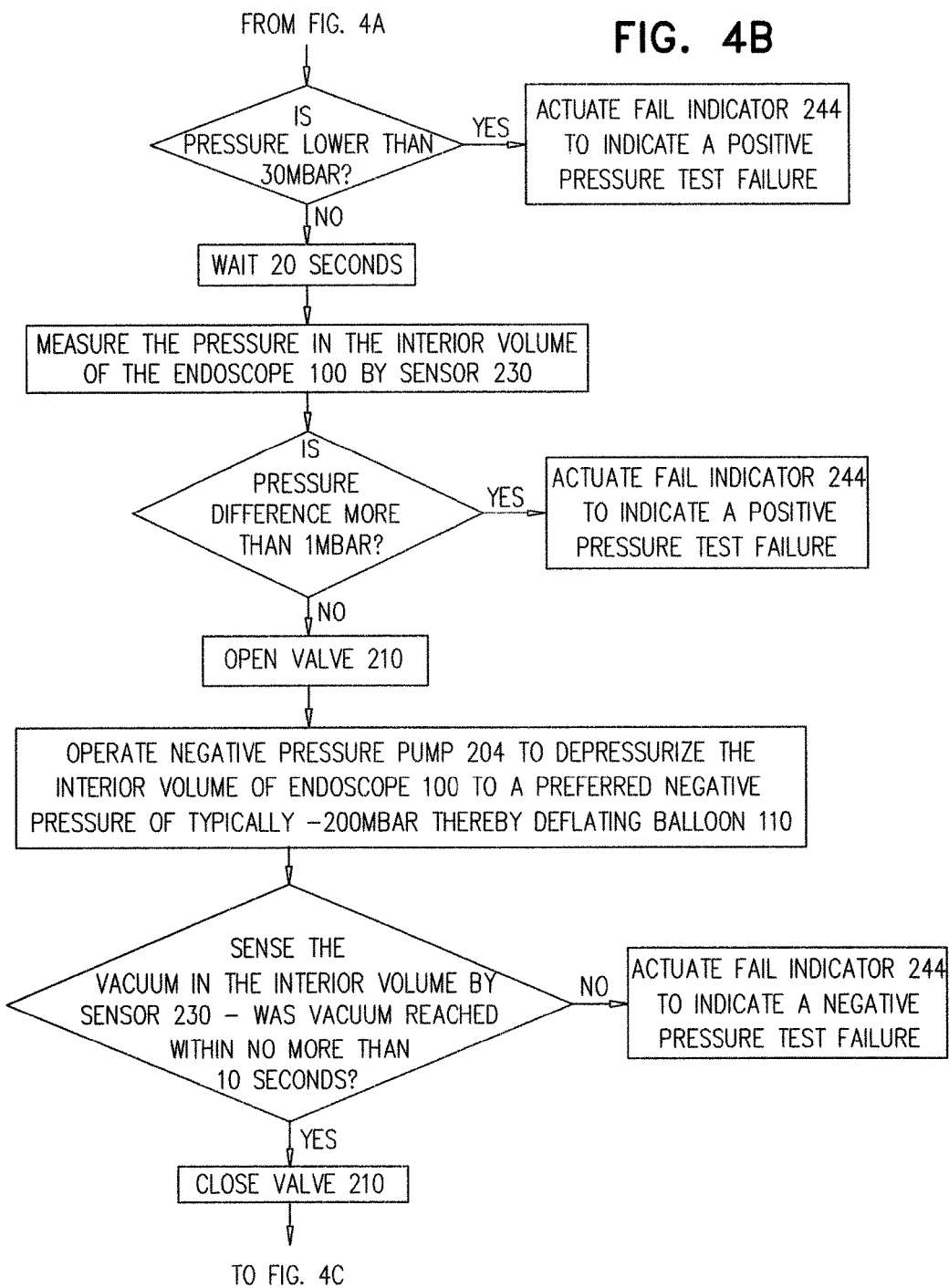

Reference is now made to FIGS. 4A-4C, which are together a simplified flow chart of the operation of the leak tester of FIG. 3 in accordance with one embodiment of the present invention.

As seen in FIGS. 4A-4C, an initial step is to sealingly couple leak test port coupler 200 to the leak test port 106 of endoscope 100, such that the interior volume 114 of the endoscope 100 is in fluid communication with the leak tester 126.

Thereafter, all of valves 208, 210 and 232 (FIG. 3) are opened in order to couple the interior volume of the endoscope to ambient pressure via the leak tester 126. Once the interior volume 114 of the endoscope 100 reaches ambient pressure, sensor 230 is calibrated accordingly.

Thereafter, valves 210 and 232 are closed and the positive pressure pump 202 is operated by controller 220 to pressurize the interior volume of endoscope 100 to a preferred pressure of typically 50 mbar, as sensed by sensor 230, thereby to inflate balloon 110 of endoscope 100. If, however, the preferred pressure of typically 50 mbar is not realized within 10 seconds of onset of pressurization, a positive pressure test failure indication is provided by controller 220, which actuates FAIL indicator 244 accordingly.

If positive pressure test failure is not indicated at this stage, an optional step can be performed by computerized controller 220, which employs readings from sensor 230 to sense and analyze the profile of pressure change over time in the interior volume of the endoscope during pressurization of the interior volume, and thereby determines whether a conventional non-balloon endoscope or a balloon endoscope is connected to leak test port coupler 200.

For example, if a balloon endoscope is connected to the leak tester 126, it will take a longer time to pressurize the interior volume of the endoscope to a preset pressure compared to a non-balloon endoscope, due to the additional volume of the balloon to be pressurized as well. Additionally, following pressurization of a balloon endoscope having an elastic balloon, the pressure will decrease over time due to balloon expansion, while this pressure change profile will not take place in a non-balloon endoscope.

If this optional step is performed and it is thus ascertained that a non-balloon endoscope is being leak-tested, then a conventional leak testing procedure will be performed, as in prior art positive pressure leak testers which employ positive pressure of typically 200 mbars. If, however, it is ascertained that a balloon endoscope is being leak-tested, then a balloon endoscope leak testing procedure will be performed, as described below.

In accordance with an embodiment of the present invention, mechanical shutter 122 is employed, prior to leak testing of balloon endoscope 100, to seal aperture 116 as described hereinabove with reference to step B in FIG. 1C. This will cause leak tester 126 to identify the balloon endoscope 100 as a non-balloon endoscope, and to perform conventional positive pressure leak testing of endoscope 100. It is appreciated that alternatively, sealing of aperture 116 allows performance of leak testing of balloon endoscope 100 by a conventional prior art leak tester, employing relatively high positive pressure of 200 mbar, without bursting or damaging balloon 110.

At this stage, the pressure in the interior volume of the endoscope 100 is monitored again, after typically a further 25 seconds. If the pressure after 25 seconds has fallen to below a preferred threshold of typically 30 mbar, a positive pressure test failure indication is provided by controller 220, which actuates FAIL indicator 244 accordingly. It is a particular feature of the present invention that the procedure described in this paragraph accommodates and takes into account possible further expansion of the balloon 110, as a result of its mechanical and elastic characteristics. Such further expansion of balloon 110 over time during the leak testing procedure may result in reduction of the pressure monitored by sensor 230, and is not be mis-construed as a leak in balloon endoscope 100. Such a procedure is not applicable to non-balloon endoscopes.

If positive pressure test failure is not indicated at this stage, the pressure in the interior volume 114 of the endoscope 100 is monitored again, after typically a further 20 seconds. If the pressure after this further 20 seconds has fallen by more than 1 mbar, a positive pressure test failure indication is provided by controller 220, which actuates FAIL indicator 244 accordingly.

If positive pressure test failure is not indicated at this stage, negative pressure leak testing is initiated, typically by opening valve 210, while maintaining valve 208 and valve 232 in a closed state, and operating negative pressure pump 204 to depressurize the interior volume of endoscope 100 to a preferred negative pressure of typically −200 mbar, as sensed by sensor 230, and thereby to deflate balloon 110 of endoscope 100. Optionally, if, the preferred pressure of typically −200 mbar is not realized within 10 seconds of onset of depressurization, a negative pressure test failure indication is provided by controller 220, which actuates FAIL indicator 244 accordingly.

If negative pressure test failure is not indicated at this optional stage, valve 232 is closed and then the negative pressure in the interior volume of the endoscope 100 is monitored again, after typically 20 seconds. If the negative pressure after 20 seconds has increased to above a preferred threshold of typically −150 mbar, a negative pressure test failure indication is provided by controller 220, which actuates FAIL indicator 244 accordingly.

If negative pressure test failure is not indicated at this stage, the pressure in the interior volume of the endoscope 100 is monitored again, after typically a further 20 seconds. If the pressure after this further 20 seconds has increased by more than 2 mbar, a negative pressure test failure indication is provided by controller 220, which actuates FAIL indicator 244 accordingly.

If negative pressure test failure is not indicated at this stage, a positive and negative pressure test success indication is provided by controller 220, which actuates PASS indicator 242 accordingly.

It is a particular feature of an embodiment of the present invention that at this stage, coupler 200 is preferably disengaged from the normally-closed leak test port 106 of endoscope 100, which maintains the interior volume of the endoscope under negative pressure and the balloon 110 in a deflated state. This feature is not necessary with non-balloon endoscopes. Preferably, deflation of balloon 110 is performed by depressurizing the interior volume of endoscope 100 to a negative pressure in the range of −5 mbar to −300 mbar. More preferably, deflation of balloon 110 is performed by depressurizing the interior volume of endoscope 100 to a negative pressure in the range of −100 mbar to −250 mbar. According to a most preferred embodiment of the present invention, the balloon 110 is deflated to a negative pressure below −150 mbar.

It is a particular feature of the present invention that the negative pressure testing procedure described hereinabove is provided.

It is a further particular feature of the present invention that the negative pressure which is maintained in the interior volume of the endoscope following the negative pressure leak testing procedure described hereinabove is sufficiently low to maintain negative pressure in the interior volume of the endoscope during reprocessing at elevated temperatures, which cause a reduction in the vacuum level in the interior volume of the endoscope being reprocessed.

Particularly, the interior volume of a balloon endoscope being reprocessed at an elevated temperature of 60 degrees Celsius, should preferably be maintained at a negative pressure lower than −150 mbar when at ambient temperature prior to reprocessing.

It is appreciated that alternatively the negative pressure testing may take place prior to the positive pressure testing. It is also appreciated that a single pump may alternatively be used to provide both pressurization and depressurization of the interior volume of the endoscope 100. It is further appreciated that leak tester 126 is suitable for leak testing of both non-balloon and balloon endoscopes.

Figure 5A:
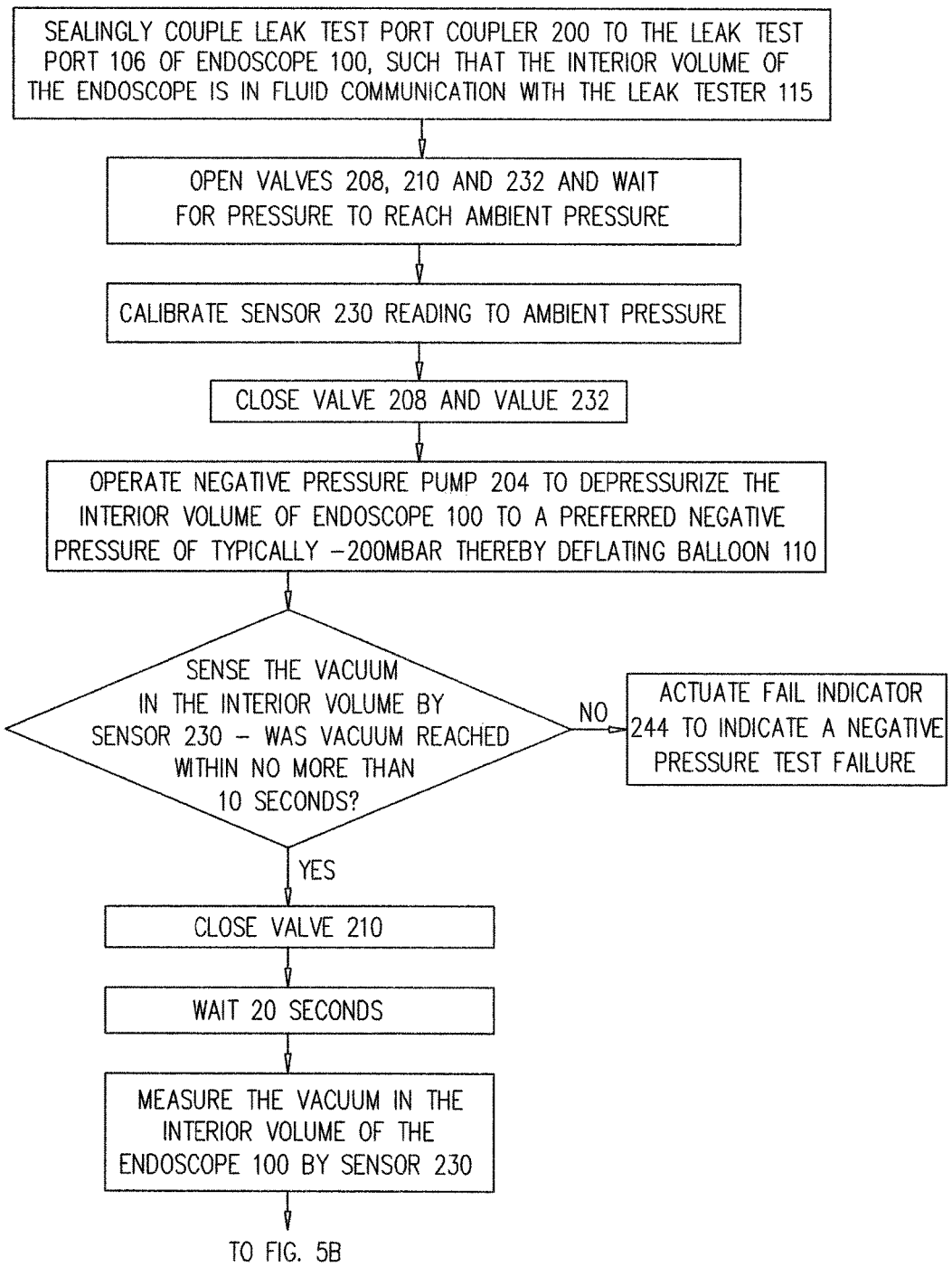

Reference is now made to FIGS. 5A and 5B, which are together a simplified flow chart of the operation of the leak tester of FIG. 3 in accordance with another embodiment of the present invention.

As seen in FIGS. 5A and 5B, an initial step is to sealingly couple leak test port coupler 200 to the leak test port 106 of endoscope 100, such that the interior volume of the endoscope is in fluid communication with the leak tester 119.

Thereafter, all of valves 208, 210 and 232 (FIG. 3) are opened in order to couple the interior volume of the endoscope to ambient pressure via the leak tester 126. Once the interior volume of the endoscope 100 reaches ambient pressure, sensor 230 is calibrated accordingly.

Thereafter, negative pressure leak testing is initiated, typically by closing valves 208 and 232 and operating negative pressure pump 204 to depressurize the interior volume 114 of endoscope 100 to a preferred negative pressure of typically −200 mbar, as sensed by sensor 230, and thereby to deflate balloon 110 of endoscope 100. Optionally, if the preferred pressure of typically −200 mbar is not realized within 10 seconds of onset of depressurization, a negative pressure test failure indication is provided by controller 220, which actuates FAIL indicator 244 accordingly.

If negative pressure test failure is not indicated at this optional stage, valve 210 is closed and then the negative pressure in the interior volume of the endoscope 100 is monitored again, after typically 20 seconds. If the negative pressure after 20 seconds has increased to above a preferred threshold of typically −150 mbar, a negative pressure test failure indication is provided by controller 220, which actuates FAIL indicator 244 accordingly.

If negative pressure test failure is not indicated at this stage, the pressure in the interior volume of the endoscope 100 is monitored again, after typically a further 20 seconds. If the pressure after this further 20 seconds has increased by more than 2 mbar, a negative pressure test failure indication is provided by controller 220, which actuates FAIL indicator 244 accordingly.

If negative pressure test failure is not indicated at this stage, a positive and negative pressure test success indication is provided by controller 220, which actuates PASS indicator 242 accordingly.

It is a particular feature of an embodiment of the present invention that at this stage, coupler 200 is preferably disengaged from the normally-closed leak test port 106 of endoscope 100, which maintains the interior volume of the endoscope under negative pressure and the balloon 110 in a deflated state. This feature is not necessary with non-balloon endoscopes. Preferably, deflation of balloon 110 is performed by depressurizing the interior volume of endoscope 100 to a negative pressure in the range of −5 mbar to −300 mbar. More preferably, deflation of balloon 110 is performed by depressurizing the interior volume of endoscope 100 to a negative pressure in the range of −100 mbar to −250 mbar.

According to a most preferred embodiment of the present invention, the balloon 110 is deflated to a negative pressure below −150 mbar.

It is a particular feature of the present invention that the negative pressure testing procedure described hereinabove is provided.

It is a particular feature of the present invention that the negative pressure which is maintained in the interior volume of the endoscope following the negative pressure leak testing procedure described hereinabove is sufficiently low to maintain negative pressure in the interior volume of the endoscope during reprocessing at elevated temperatures, which cause a reduction in the vacuum level in the interior volume of the endoscope being reprocessed.

Particularly, the interior volume of a balloon endoscope being reprocessed at an elevated temperature of 60 degrees Celsius, is preferably maintained at a negative pressure lower than −150 mbar when at ambient temperature prior to reprocessing.

It is further appreciated that leak tester 126 is suitable for leak testing of both non-balloon and balloon endoscopes.

Figure 6:
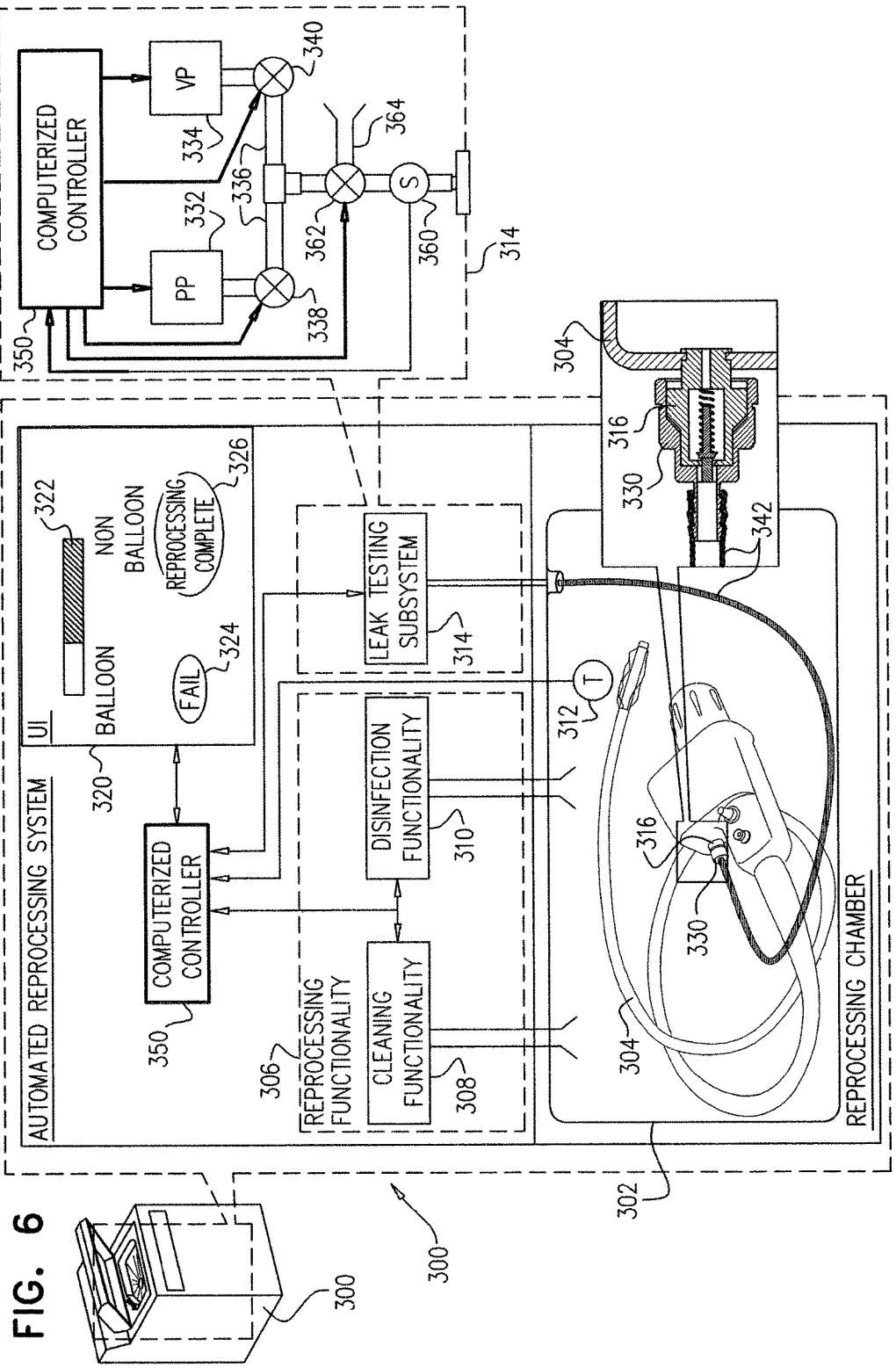
FIG. 6 is a simplified system block diagram illustration of an automated reprocessing system constructed and operative in accordance with a preferred embodiment of the present invention.

Reference is now made to FIG. 6, which is a simplified system block diagram illustration of an automated reprocessing system 300 constructed and operative in accordance with a preferred embodiment of the present invention.

As seen in FIG. 6, the automated reprocessing system preferably includes a reprocessing chamber 302 in which an endoscope 304 to be reprocessed is located during reprocessing. The endoscope can be a conventional non-balloon endoscope, such as an EC 3890i colonoscope, commercially available from Pentax Europe GmbH, of 104 Julius-Vosseler St., 22527 Hamburg, Germany, or a balloon endoscope, such as a G-EYE™ 3890i colonoscope, commercially available from Smart Medical Systems, of Raanana, Israel.

Reprocessing functionality 306, which may be entirely conventional and typically comprises a fluids supply subsystem including endoscope cleaning functionality 308 and endoscope disinfection functionality 310, is operatively associated with the reprocessing chamber 302. A temperature sensor 312 is preferably located within the reprocessing chamber 302 for measuring the temperature of cleaning and or disinfecting fluids located therein at any or all times during reprocessing.

In accordance with a preferred embodiment of the present invention a leak testing subsystem 314 is provided for communication with a leak test port 316 of endoscope 304. It is a particular feature of the present invention that the leak testing subsystem 314 provides negative pressure leak testing functionality, which is important for balloon endoscopes and may also be used for non-balloon endoscopes.

It is a further particular feature of the present invention that the leak testing subsystem 314 provides balloon deflation control functionality which is operative to maintain the interior volume of the balloon in a negative pressure state during at least part of operation of the automated balloon endoscope reprocessing functionality 306, and preferably during all of the operation of the automated balloon endoscope reprocessing functionality 306.

A user interface 320 (denoted by UI in FIG. 6) is preferably provided which includes an operator engageable switch 322, enabling an operator to select a reprocessing mode suitable for a balloon endoscope or a reprocessing mode suitable for a non-balloon endoscope. The user interface 320 preferably also includes an indicator 324 which alerts the operator to a leak test failure as well as an indicator 326, which informs the operator that reprocessing of endoscope 304 has been successfully completed.

The leak testing subsystem 314 preferably includes a leak test port coupler 330, which is adapted to connect with leak test port 316 of a conventional non-balloon endoscope or a conventional balloon endoscope.

A positive gas pressure source, such as an air pressure pump 332 and a negative gas pressure source, such as a vacuum pump 334 are preferably connected to leak test port coupler 330 via a manifold 336 and automatically controllable valves 338 and 340 and a flexible tube 342. A computerized controller 350 is operative to control the operation of pumps 332 and 334 and/or valves 338 and 340 in order to apply at different times, positive pressure and negative pressure to the leak test port 316 of endoscope 304 via the leak test port coupler 330. Alternatively, a single pump providing at different times, positive and negative pressure may be employed. An example of such a pump is model 250 EC, commercially available from Schwarzer Precision GmbH+ Co. KG of Am Lichtbogen 7, 45141 Essen, Germany.

Preferably, computerized controller 350 also controls the operation of other components and functionalities of automated reprocessing system 300, such as the operation of the reprocessing functionality 306, and is coordinating the relative timing of operation of the fluid supply subsystem and the leak testing subsystem.

A computerized pressure sensor 360 is preferably coupled to leak test port coupler 330 and is also coupled to pumps 332 and 334 via a valve 362 and is configured to sense changes in pressure over time at the leak test port of the endoscope both at a time when the leak test port is under positive pressure and at a time when the leak test port is under negative pressure.

Preferably, valve 362 is an automatically controllable two-state valve, which can be positioned in either an "open" state in which it connects tube 342 and manifold 336 to the ambient via a purge tube 364, and a "closed" state in which it connects manifold 336 and tube 342 to each other while disconnecting them from purge tube 364 and preventing air communication with the ambient.

In accordance with a preferred embodiment of the present invention, the computerized controller 350 cooperates with the computerized pressure sensor 360 to carry out a negative pressure leak test protocol, two examples of which are described hereinbelow with reference to FIGS. 7A-7B and 8A-8C.

Figure 7A:
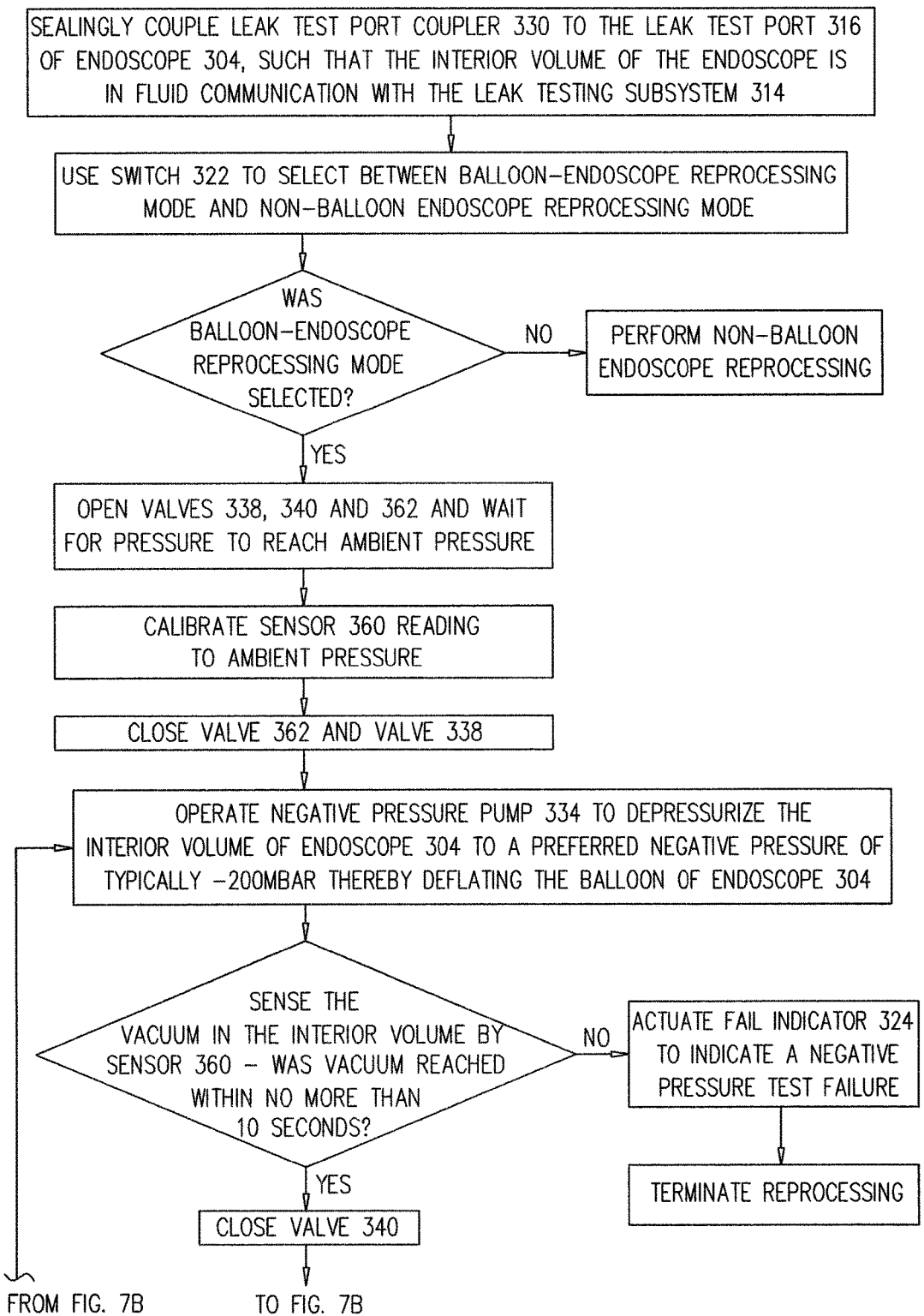
FIGS. 7A and 7B are together a simplified flow chart of the operation of the reprocessing system of FIG. 6 in accordance with one embodiment of the present invention.
Figure 7B:
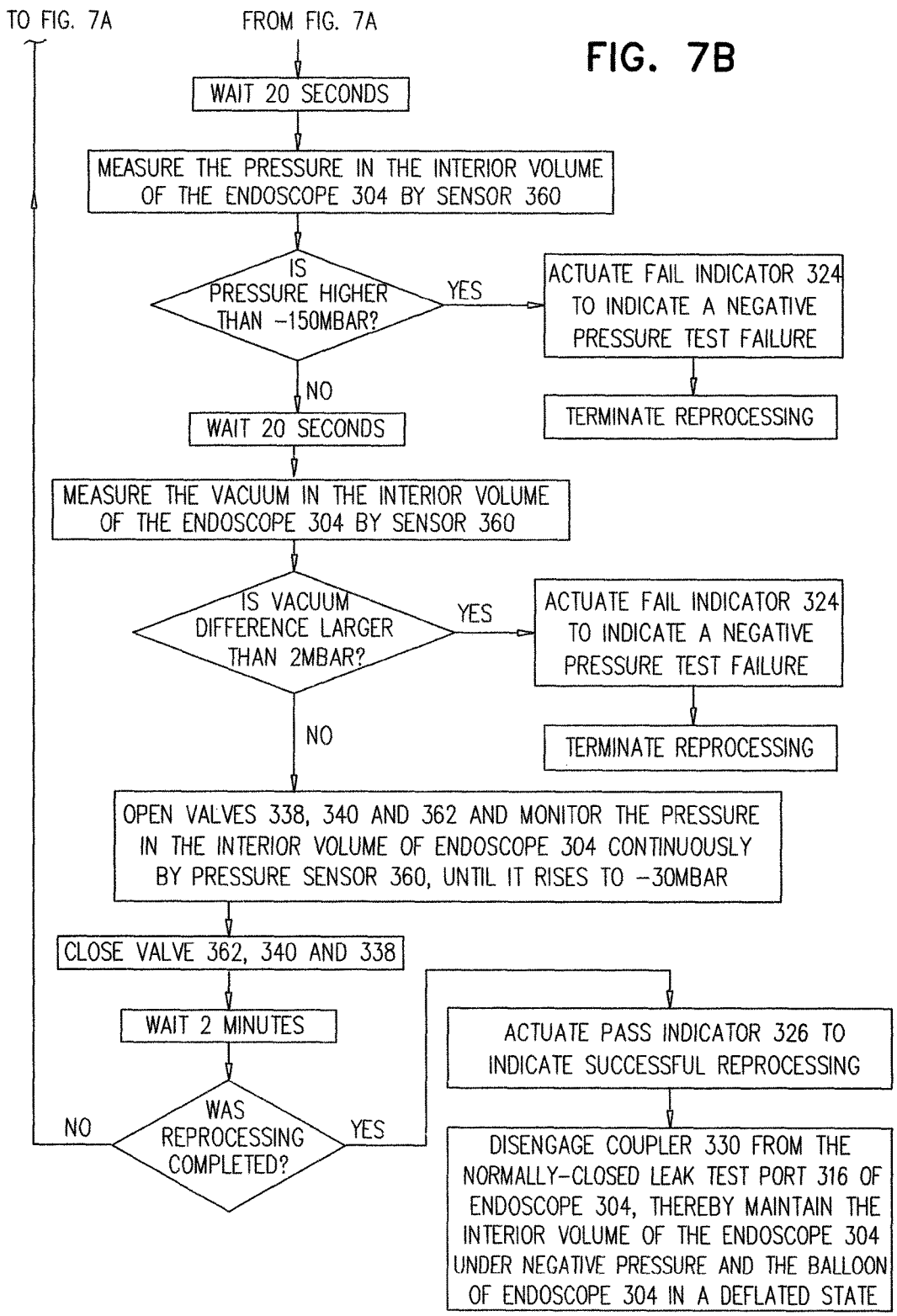

Reference is now made to FIGS. 7A and 7B, which are together a simplified flow chart of the operation of the reprocessing system of FIG. 6 in accordance with one embodiment of the present invention.

As seen in FIGS. 7A and 7B, an initial step is to sealingly couple leak test port coupler 330 to the leak test port 316 of endoscope 304, such that the interior volume of the endoscope is in fluid communication with the leak testing subsystem 314.

Thereafter, the operator preferably uses switch 322 to select the suitable reprocessing mode for the endoscope being reprocessed. If a non-balloon reprocessing mode is selected, automated reprocessing system 300 perform a conventional, non-balloon endoscope reprocessing procedure, such as performed in prior art automated reprocessing systems.

In accordance with an embodiment of the present invention, endoscope 304 being reprocessed is the balloon endoscope 100 described hereinabove with reference to FIGS. 1A-2, which includes balloon 110, aperture 116 that normally enables air flow between the interior volumes of balloon 110 and endoscope 100, and mechanical shutter 122 which can be employed to seal aperture 116.

In accordance with this embodiment of the present invention, the mechanical shutter 122 is employed, prior to reprocessing of balloon endoscope 100 by automated reprocessing system 300, to seal aperture 116 as described hereinabove with reference to step B in FIG. 1C, and the operator uses switch 322 to select a non-balloon endoscope reprocessing mode. Thus, automated reprocessing machine 300 is employed to perform conventional reprocessing which may include positive pressure leak testing of balloon endoscope 100, without bursting or damaging balloon 110. It is appreciated that alternatively, sealing of aperture 116 allows conventional reprocessing of balloon endoscope 100 by a conventional prior art automated reprocessing machine that employs relatively high positive pressure while monitoring leaks during the reprocessing procedure, without bursting or damaging balloon 110.

In the description which follows, it is assumed, unless explicitly indicated otherwise, that reprocessing of a balloon endoscope is selected, which balloon endoscope reprocessing is a particular feature of the present invention.

Thereafter, under the control of computerized controller 350, all of valves 338, 340 and 362 (FIG. 6) are opened in order to couple the interior volume of the endoscope to ambient pressure via the leak testing subsystem 314. Once the interior volume of endoscope 304 reaches ambient pressure, pressure sensor 360 is calibrated accordingly.

Negative pressure leak testing is initiated, typically by closing valves 338 and 362 and operating negative pressure pump 334 to depressurize the interior volume of endoscope 304 to a preferred negative pressure of typically −200 mbar, as sensed by pressure sensor 360, and thereby to deflate the balloon of endoscope 304. Optionally, if the preferred pressure of typically −200 mbar is not realized within 10 seconds of onset of depressurization, a negative pressure test failure indication is provided by controller 350, which actuates FAIL indicator 324 accordingly and terminates reprocessing. If negative pressure test failure is not indicated at this optional stage, valve 340 is closed and then the negative pressure in the interior volume of the endoscope 304 is monitored again, after typically 20 seconds. If the negative pressure after 20 seconds has increased to above a preferred threshold of typically −150 mbar, a negative pressure test failure indication is provided by controller 350, which actuates FAIL indicator 324 accordingly and terminates reprocessing.

If negative pressure test failure is not indicated at this stage, the pressure in the interior volume of the endoscope 304 is monitored again, after typically a further 20 seconds. If the pressure after this further 20 seconds has increased by more than 2 mbar, a negative pressure test failure indication is provided by controller 350, which actuates FAIL indicator 324 and terminates reprocessing accordingly.

If negative pressure test failure is not indicated at this stage, preferably all of valves 338, 340 and 362 (FIG. 6) are opened and the pressure in the interior volume of the endoscope 304 is monitored continuously by pressure sensor 360. Once the pressure in the interior volume of the endoscope 304, as measured by pressure sensor 360, rises, to typically −30 mbar, valves 338, 340 and 362 are closed in order to maintain this negative pressure in the interior volume of endoscope 304.

Preferably, deflation of the balloon of balloon endoscope 304, during and in between leak testing cycles, is performed and maintained by depressurizing the interior volume of endoscope 304 to a negative pressure in the range of −5 mbar to −300 mbar. More preferably, deflation of the balloon of balloon endoscope 304, during and in between leak testing cycles, is performed and maintained by depressurizing the interior volume of endoscope 304 to a negative pressure in the range of −100 mbar to −250 mbar. According to a preferred embodiment of the present invention, the balloon of balloon endoscope 304 is deflated to a negative pressure below −150 mbar.

It is a particular feature of an embodiment of the present invention that leak testing of a balloon endoscope takes place when the interior volume of the endoscope is at a relatively strong vacuum, typically between −150 mbar and −200 mbar and the remainder of the reprocessing procedure takes place when the interior volume of the endoscope is at a relatively weak vacuum, typically between −10 mbar and −50 mbar, and preferably −30 mbar.

Preferably, the foregoing negative leak test procedure is repeated at generally regular intervals during reprocessing, such as every 2-5 minutes.

Once reprocessing has been successfully completed in the absence of any negative pressure leak test failures, a successful reprocessing indication is provided by controller 350, which actuates indicator 326 accordingly.

It is a particular feature of an embodiment of the present invention that at this stage, coupler 330 is preferably disengaged from the normally-closed leak test port 316 of endoscope 304, which maintains the interior volume of the endoscope under negative pressure and the balloon of balloon endoscope 304 in a deflated state. It is appreciated that storage of balloon-endoscope 304 with a deflated balloon may be beneficial for protecting the balloon from mishandling and puncture, as well as for enabling placement of a protective cover over the balloon. This feature is not necessary with non-balloon endoscopes.

Figure 8A:
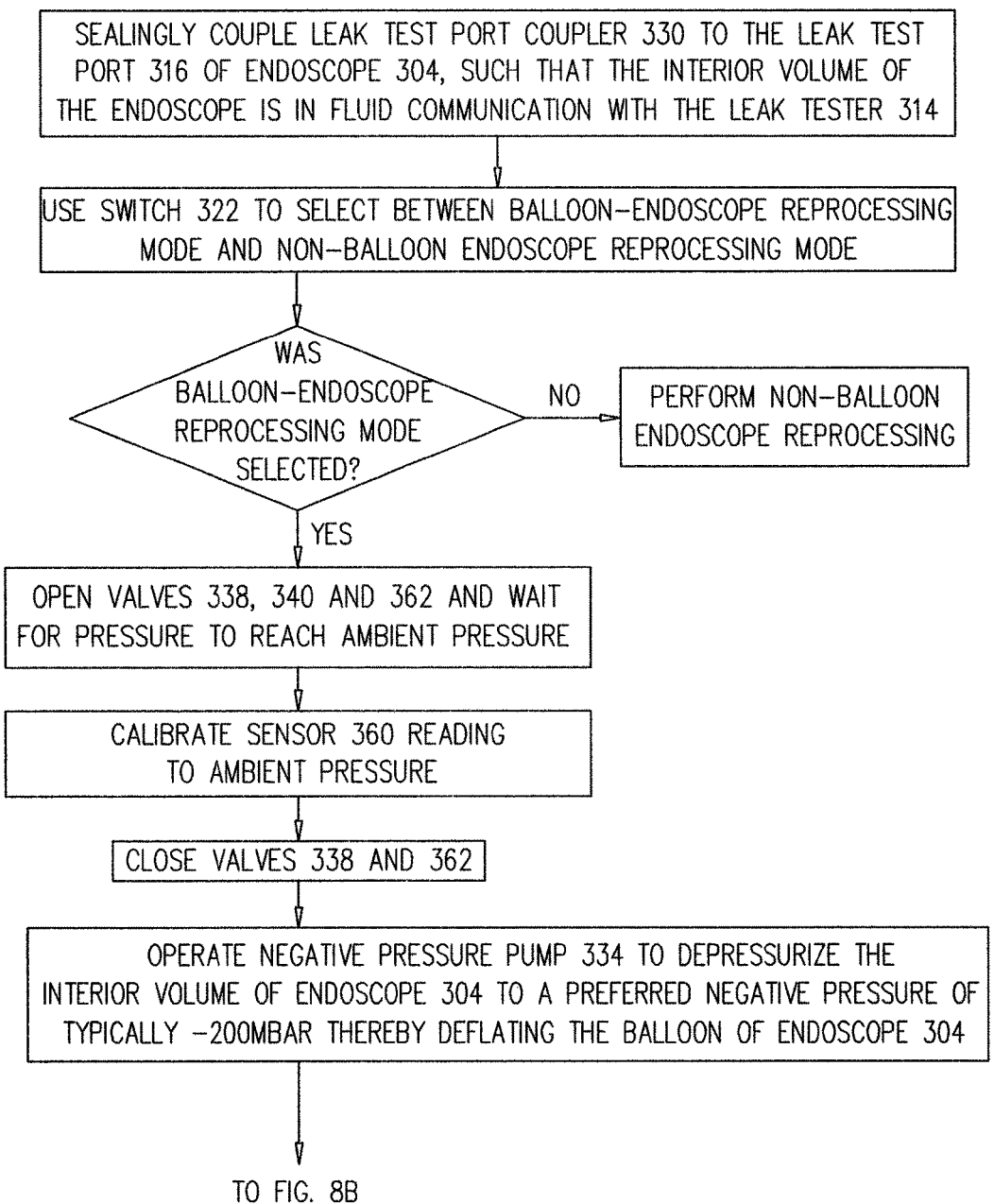
Figure 8B:
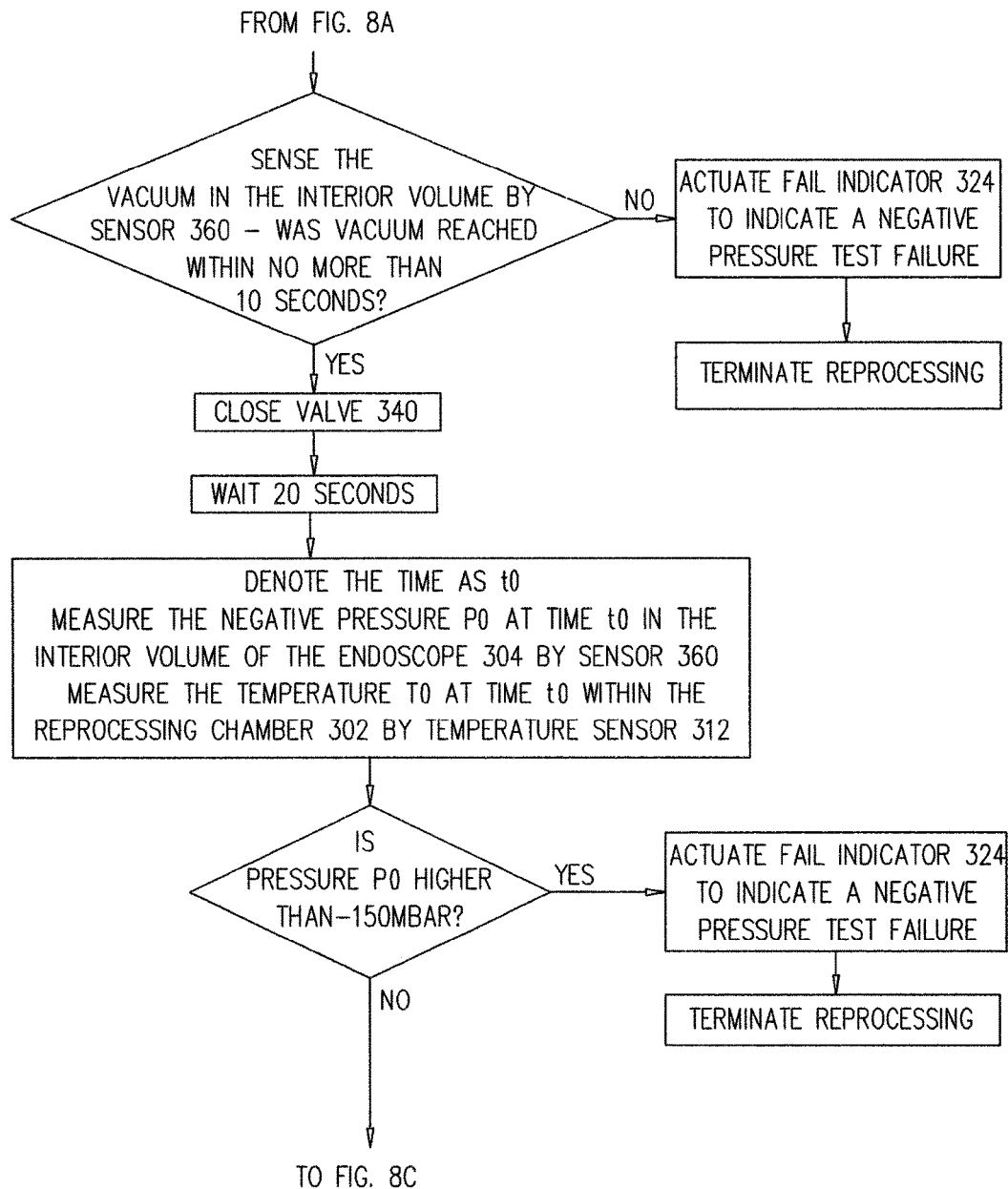

Reference is now made to FIGS. 8A-8C, which are together a simplified flow chart of the operation of the reprocessing system of FIG. 6 in accordance with another embodiment of the present invention.

As seen in FIGS. 8A-8C, an initial step is to sealingly couple leak test port coupler 330 to the leak test port 316 of endoscope 304, such that the interior volume of the endoscope is in fluid communication with the leak testing subsystem 314.

Thereafter, the operator preferably uses switch 322 to select the suitable reprocessing mode for the endoscope being reprocessed. If a non-balloon reprocessing mode is selected, automated reprocessing system 300 perform a conventional, non-balloon endoscope reprocessing procedure, such as performed in prior art automated reprocessing systems. In the description which follows, it is assumed, unless explicitly indicated otherwise, that reprocessing of a balloon endoscope is selected, which balloon endoscope reprocessing is a particular feature of the present invention.

Thereafter, under the control of computerized controller 350, all of valves 338, 340 and 362 (FIG. 6) are opened in order to couple the interior volume of the endoscope to ambient pressure via the leak testing subsystem 314. Once the interior volume of the endoscope 304 reaches ambient pressure, pressure sensor 360 is calibrated accordingly.

Negative pressure leak testing is initiated, typically by closing valves 338 and 362 and operating negative pressure pump 334 to depressurize the interior volume of endoscope 304 to a preferred negative pressure of typically −200 mbar, as sensed by pressure sensor 360, and thereby to deflate the balloon of endoscope 304. Optionally, if the preferred pressure of typically −200 mbar is not realized within 10 seconds of onset of depressurization, a negative pressure test failure indication is provided by controller 350, which actuates FAIL indicator 324 accordingly and terminates reprocessing.

If negative pressure test failure is not indicated at this optional stage, valve 340 is closed and then, after typically 20 seconds, at a time designated t0, the negative pressure in the interior volume of the endoscope 304 is again monitored by pressure sensor 360 and the temperature within the reprocessing chamber 302 is measured by temperature sensor 312. The measured negative pressure at this stage, at time t0, is designated P0 and the measured temperature at t0 is designated T0.

If the negative pressure P0 is higher than a preferred threshold of typically −150 mbar, a negative pressure test failure indication is provided by controller 350, which actuates FAIL indicator 324 accordingly and terminates reprocessing.

If negative pressure test failure is not indicated at this stage, the pressure in the interior volume of the endoscope 304 and the temperature within the reprocessing chamber 302 are monitored again at time t, after a time interval from t0 denoted by Dt, which is dictated by computerized controller 350. If periodical intermittent leak monitoring is required, time interval Dt may be a predetermined time interval such as a generally short time interval in the range of 1-60 seconds or a generally longer time interval in the range of 1-5 minutes. Alternatively, if continuous leak monitoring is desired such that leak sensing cycles are performed immediately one after the other, time interval Dt may be the electronic clock time unit of computerized controller 350 or a multiplicity thereof.

It is appreciated that even in the absence of a leak, the vacuum within the interior volume of the endoscope 304 is weakened as a function of temperature increase.

It is further appreciated that the vacuum within the interior volume of the endoscope 304 may be weakened very slowly as a function of elapsed time due to imperfections in sealing between various components which are maintained under vacuum and this weakening is not indicative of an unacceptable leak in the balloon endoscope, which should be identified as a leak test failure.

Accordingly, controller 350 sets an acceptable negative pressure threshold PT(t) which varies as a function of temperature as measured by temperature sensor 312 and as a function of elapsed time from time to. Should the pressure P(t) measured by sensor 360 at any given time t exceed the corresponding acceptable negative pressure threshold PT(t), a failure will be indicated.

The negative pressure threshold PT(t) at a time t, measured at a given time after time t0, is preferably given by the following general expression:

$$PT(t)=F(Tt,T0,t,t0,P0),$$

F being a function of Tt, T0, t, t0 and P0, where:

Tt is the temperature of the interior of the reprocessing chamber 302 at time t, as measured by temperature sensor 312;

T0 is the temperature of the interior of the reprocessing chamber 302 at time t0, as measured by temperature sensor 312; and P0 is the negative pressure in the interior volume of the endoscope 304 at time t0, as measured by pressure sensor 360.

In accordance with a preferred embodiment of the present invention, F(Tt, T0, t, t0, P0) is embodied in a predetermined calibration table, which is stored in computerized controller 350. Controller 350 retrieves the appropriate negative pressure threshold PT(t) for each set of specific values of Tt, T0, t, t0 and P0.

It is appreciated that if the temperature profile in the reprocessing chamber throughout the reprocessing procedure, as measured by temperature sensor 312, is known a priori, such as by employing a predetermined heating profile for the solutions employed throughout the reprocessing procedure, then PT(t) can be calculated or retrieved as a function of P0 and t, and actual measurement of the temperature T(t) by temperature sensor 312 may be obviated.

More particularly in accordance with a preferred embodiment of the present invention, negative pressure threshold PT(t) at a given time t is expressed by the following function:

$$PT(t)=F1(Tt,T0,P0)+F2(t-t0)$$

where:

F1 is a function of the relationship between Tt, the temperature measured by temperature sensor 312 at a given time t, and T0 and P0, the respective temperature measured by temperature sensor 312 and pressure measured by pressure sensor 360 at time t0; and F2 is a function of the elapsed time from time t0 to t.

Preferably, F1 is given by the expression: $F1=(Tt/T0) \cdot P0$, where Tt and T0 are measured in degrees Kelvin and P0 is measured in the absolute pressure units above zero pressure, such as mbar or atmospheres, as used for PT(t).

Preferably, F2 is given by the expression: $F2=K \cdot (t-t0)$, where K is a constant, expressing change in pressure over time. In accordance with a preferred embodiment of the present invention, K is in the range of 0.01-0.20 mbar per second. In accordance with a more preferred embodiment of the present invention, K is in the range of 0.02-0.10 mbar per second. In accordance with a presently most preferred embodiment of the present invention, K is approximately 0.05 mbar per second.

The pressure P(t) and the temperature T(t) at time t are measured by respective pressure sensor 360 and temperature sensor 312 continuously or intermittently as appropriate. Should the measured negative pressure P(t) be higher than the negative pressure threshold PT(t) a negative pressure test failure indication is provided by controller 350, which actuates FAIL indicator 324 accordingly and terminates reprocessing.

Once reprocessing has been successfully completed in the absence of any negative pressure leak test failures, a successful reprocessing indication is provided by controller 350, which actuates indicator 326 accordingly.

It is a particular feature of an embodiment of the present invention that at this stage, coupler 330 is preferably disengaged from the normally-closed leak test port 316 of endoscope 304, which maintains the interior volume of the endoscope under negative pressure and the balloon of balloon endoscope 304 in a deflated state. It is appreciated that storage of balloon-endoscope 304 with a deflated balloon may be beneficial for protecting the balloon from mishandling and puncture, as well as for enabling placement of a protective cover over the balloon. This feature is not necessary with non-balloon endoscopes.

Reference is now made to FIGS. 9A and 9B, which are simplified illustrations of a reprocessing method operative in accordance with another preferred embodiment of the present invention.

As seen in 9A and 9B, there is provided a reprocessing method for a balloon endoscope; which is particularly characterized in that it includes:

inflating a balloon of a balloon endoscope to a positive pressure state following clinical use thereof;

thereafter, cleaning and/or disinfecting the outer surface of the balloon while the balloon is inflated in a positive pressure state;

thereafter, deflating the balloon of the balloon endoscope to a negative pressure state; and thereafter maintaining the interior of the balloon in a negative pressure state during at least part of reprocessing said balloon endoscope.

There is also provided a method for reprocessing a balloon endoscope having a balloon interior volume and an endoscope interior volume which are normally in fluid communication via at least one aperture, the method comprising sealing the at least one aperture during at least part of reprocessing of the balloon endoscope.

FIGS. 9A and 9B illustrate steps carried out in an endoscopy room. Step A, shown in FIG. 9A, illustrates a balloon endoscope 400, such as a model G-EYE™ 3890i colonoscope, commercially available from Smart Medical Systems of Raanana, Israel, after having been removed from the body of a patient following an endoscopic procedure, such as a colonoscopy. At this stage, the balloon of the balloon endoscope 400 may be inflated or deflated.

During the endoscopic procedure and immediately thereafter at Steps A, B and C, the balloon endoscope 400 is operatively connected with an inflation/deflation system 402, such as a SPARK2C inflation system, commercially available from Smart Medical Systems of Raanana, Israel. Specifically a flexible inflation/deflation tube 404 is sealingly connected at one end thereof to a normally-closed leak-test port 406 of balloon endoscope 400, as seen in enlargement B, and is sealingly connected at an opposite end thereof to an inflation/deflation tube connection port 408 of the inflation/deflation system 402.

As further seen in FIGS. 9A and 9B, balloon endoscope 400 includes a balloon 410 at its forward portion, which is sealingly mounted over an outer sheath 412 of balloon endoscope 400. An interior volume 413 of balloon 410 is normally in fluid communication with an interior volume 414 of balloon endoscope 400, via at least one aperture 416 formed in the outer sheath 412 of the endoscope 400. It is thus appreciated that balloon 410 may be inflated and deflated by inflation/deflation system 402 via flexible inflation/deflation tube 404, leak test port 406, interior volume 414 of balloon endoscope 400, and at least one aperture 416, altogether forming a continuous fluid communication path between inflation/deflation system 402 and the interior volume 413 of balloon 410.

It is appreciated that the volume of balloon endoscope 400 interiorly of outer sheath 412 may contain various conduits and channels (not shown) passing therethrough, such as optical and illumination bundles, electronics, steering wires, an instrument channel, and other components as appropriate. It is appreciated that inflation/deflation air can flow freely through the interior volume 414, which is the volume interior to outer sheath 412 that is not occupied by such conduits and channels.

In step B, shown in FIG. 9A, it is seen that if the balloon 410 of the endoscope 400 is not already fully inflated, the operator presses on an inflate control button 417 of an inflation/deflation control unit 418 of the inflation/deflation system 402 to cause the inflation/deflation system 402 to fully inflate the balloon 410. At this stage, the inflated balloon 410 is cleaned and/or disinfected, such as by immersing balloon 410 in cleaning and/or disinfecting solutions and wiping it with a soft sponge or cloth, as shown in enlargement A, or by any other suitable cleaning and/or disinfecting procedure.

In step C, shown in FIG. 9A, it is seen that following the cleaning and/or disinfecting of balloon 410 while it is in an inflated state, the operator presses on a deflate control button 419 of the inflation/deflation control unit 418 of the inflation/deflation system 402 to cause the inflation/deflation system 402 to fully deflate the balloon 410, as seen in enlargement C.

It is a particular feature of an embodiment of the present invention that deflation of the balloon 410 effects sealing, as shown in enlargement D, during at least part of reprocessing of the balloon endoscope, of the at least one aperture 416 formed in the outer sheath 412 of the endoscope 400, which aperture normally provides fluid communication between the interior volume 413 of balloon 410 and the interior volume 414 of the endoscope 400. This is important in order to ensure that any reprocessing fluids that might somehow enter the interior volume 413 of balloon 410 from the outside during reprocessing do not enter the interior volume 414 of the endoscope.

It is appreciated that such sealing, during at least part of reprocessing of the balloon endoscope, of the at least one aperture 416, could be provided otherwise than by means of deflation of the balloon 410, such as by a mechanical sealing element or shutter that blocks the at least one aperture 416 and prevents flow of fluids therethrough, as described hereinabove with reference to FIGS. 1B and 1C.

Referring now to FIG. 9B, at step D the operator disconnects the flexible inflation/deflation tube 404 from normally-closed leak-test port 406 of balloon endoscope 400. Due to the normally-closed operation of leak-test port 406, interior volume 414 of endoscope 400 remains in a vacuum state and the balloon 410 remains fully deflated.

Step E of FIG. 9B, shows subsequent shut-down of the inflation/deflation system 402.

It is a particular feature of the embodiment of the present invention described with reference to FIGS. 9A and 9B that balloon endoscope 400, while balloon 410 is in a deflated state, is disconnected from inflation/deflation system 402 while the inflation/deflation system 402 is powered on and thereby maintaining vacuum in interior volume 414 of endoscope 400 and deflation of balloon 410, and that system 402 is powered off only after its disconnection from endoscope 400.

It will be appreciated by persons skilled in the art that the present invention is not limited to what has been particularly shown and described hereinabove. Rather the scope of the invention includes both combinations and subcombinations of the various features described hereinabove as well as modifications and variations thereof which would occur to persons skilled in the art upon reading the foregoing description and which are not in the prior art.

The invention claimed is:

1. A method for reprocessing a balloon endoscope, the method comprising the steps of:
providing a balloon endoscope, the balloon endoscope including a balloon, at a forward portion of the balloon endoscope, which is sealingly mounted over an outer sheath of the balloon endoscope, an interior volume of the balloon being in fluid communication with an interior volume of the balloon endoscope via at least one aperture formed in the outer sheath of the balloon endoscope;
deflating the balloon of the balloon endoscope to a negative pressure state following clinical use thereof by applying a vacuum to said interior volume of the balloon endoscope to hold the balloon in sealing engagement with said at least one aperture;
reprocessing the balloon endoscope by providing reprocessing fluids to an exterior surface of the balloon; and
maintaining the interior volume of the balloon in the negative pressure state with the balloon held in sealing engagement with the at least one aperture during at least part of the reprocessing of said balloon endoscope so as to ensure that the reprocessing fluids do not enter the interior volume of the balloon endoscope.

2. The method for reprocessing a balloon endoscope according to claim 1 and wherein:
said reprocessing comprises cleaning; and
said maintaining the interior volume of the balloon in the negative pressure state during at least part of reprocessing said balloon endoscope includes maintaining the interior volume of the balloon in the negative pressure state during at least part of said cleaning.

3. The method for reprocessing a balloon endoscope according to claim 2 and wherein:
said cleaning includes at least automated cleaning; and
said maintaining the interior volume of the balloon in the negative pressure state during at least part of reprocessing said balloon endoscope includes maintaining the interior volume of the balloon in the negative pressure state during at least part of said automated cleaning.

4. The method for reprocessing a balloon endoscope according to claim 1 and wherein:
said reprocessing comprises disinfecting; and
said maintaining the interior volume of the balloon in the negative pressure state during at least part of reprocessing said balloon endoscope includes maintaining the interior volume of the balloon in the negative pressure state during at least part of said disinfecting.

5. The method for reprocessing a balloon endoscope according to claim 4 and wherein:
said cleaning includes at least automated disinfecting; and
said maintaining the interior volume of the balloon in the negative pressure state during at least part of reprocessing said balloon endoscope includes maintaining the interior volume of the balloon in the negative pressure state during at least part of said automated disinfecting.

6. The method for reprocessing a balloon endoscope according to claim 1 and wherein:
a normally-closed leak testing port is provided in fluid communication with said balloon endoscope; and
said maintaining the interior volume of the balloon in the negative pressure state during said at least part of reprocessing includes deflating said interior volume of said balloon endoscope through said leak testing port.

7. The method for reprocessing a balloon endoscope according to claim 6 and wherein said deflating said interior volume of said balloon endoscope through said leak testing port comprises:
coupling a negative pressure device to said leak testing port and operating said negative pressure device to apply vacuum to said interior volume of said endoscope;
thereafter, disconnecting said normally-closed leak testing port from said negative pressure device; and
maintaining, by said normally-closed leak testing port, negative pressure in said interior volume of said balloon endoscope.

8. The method for reprocessing a balloon endoscope according to claim 1 and wherein said deflating the balloon of the balloon endoscope to a negative pressure state comprises deflating said balloon to a negative pressure sufficient to maintain deflation of said balloon notwithstanding an increase in temperature encountered during said reprocessing.

9. The method for reprocessing a balloon endoscope according to claim 1 and wherein said deflating the balloon of the balloon endoscope to a negative pressure state comprises deflating said balloon to a negative pressure in the range of −5 mbar to −300 mbar.

10. The method for reprocessing a balloon endoscope according to claim 1 and wherein said deflating the balloon of the balloon endoscope to a negative pressure state comprises deflating said balloon to a negative pressure in the range of −100 mbar to −250 mbar.

11. The method for reprocessing a balloon endoscope according to claim 1 and wherein said deflating the balloon of the balloon endoscope to a negative pressure state comprises deflating said balloon to a negative pressure below −150 mbar.

12. The method for reprocessing a balloon endoscope according to claim 1 and wherein said deflating the balloon of the balloon endoscope to a negative pressure state comprises deflating said balloon to a negative pressure lower than a negative pressure threshold which negative pressure threshold varies over time during reprocessing.

13. The method for reprocessing a balloon endoscope according to claim 1 and wherein said deflating the balloon of the balloon endoscope to a negative pressure state comprises deflating said balloon to a negative pressure lower than a negative pressure threshold which varies as a function of the temperature at said balloon endoscope during said reprocessing.

14. The method for reprocessing a balloon endoscope according to claim 1 and wherein said deflating the balloon of the balloon endoscope to a negative pressure state comprises deflating said balloon to a negative pressure lower than a negative pressure threshold which varies as a function of the measured negative pressure inside said balloon at a specific time prior to or during said reprocessing.

15. The method for reprocessing a balloon endoscope according to claim 1 and wherein said deflating the balloon of the balloon endoscope to a negative pressure state comprises deflating said balloon to a negative pressure lower than a negative pressure threshold PT(t) where:

$PT(t) = F(Tt, T0, P0)$, where:
Tt is the temperature at said balloon endoscope at a time t;
T0 is the temperature at said balloon endoscope at an initial time t0; and
P0 is the pressure at said interior volume of said balloon of said balloon endoscope at said initial time t0.

16. The method for reprocessing a balloon endoscope according to claim 1 and wherein said deflating the balloon of the balloon endoscope to a negative pressure state comprises deflating said balloon to a negative pressure lower than a negative pressure threshold PT(t) where:

$PT(t) = F1(Tt, T0, P0) + F2(t-t0)$ where:
Tt is the temperature at said balloon endoscope at a time t;
T0 is the temperature at said balloon endoscope at an initial time t0;
P0 is the pressure at said interior volume of said balloon of said balloon endoscope at said initial time t0; and
F2 is a function of the elapsed time from time t0 to t.

17. The method for reprocessing a balloon endoscope according to claim 16 and wherein $F1 = (Tt/T0) - P0$, where Tt and T0 are measured in degrees Kelvin and P0 is measured in the absolute pressure units above zero pressure used for PT(t).

18. The method for reprocessing a balloon endoscope according to claim 16 and wherein $F2 = K - (t-t0)$, where K is a constant, expressing change in pressure over time.

19. The method for reprocessing a balloon endoscope according to claim 18 where K is in the range of 0.01-0.20 mbar per second.

20. The method for reprocessing a balloon endoscope according to claim 18 where K is in the range of 0.02-0.10 mbar per second.

21. The method for reprocessing a balloon endoscope according to claim 1, wherein the interior volume of the balloon is maintained in the negative pressure state when the reprocessing fluids are in contact with the exterior surface of the balloon.

22. The method for reprocessing a balloon endoscope according to claim 1, wherein at least a portion of the reprocessing of the balloon endoscope occurs at an elevated reprocessing temperature and the interior volume of the balloon is maintained in the negative pressure state throughout the elevated reprocessing temperature portion.

23. The method for reprocessing a balloon endoscope according to claim 1, wherein the interior volume of the balloon is maintained in the negative pressure state for the entirety of at least one of an automated cleaning stage or an automated disinfecting phase of the reprocessing of said balloon endoscope.

* * * * *